US006875419B2

(12) United States Patent
Sherry et al.

(10) Patent No.: US 6,875,419 B2
(45) Date of Patent: Apr. 5, 2005

(54) PARAMAGNETIC METAL ION-BASED MACROCYCLIC MAGNETIZATION TRANSFER CONTRAST AGENTS AND METHOD OF USE

(75) Inventors: A. Dean Sherry, Dallas, TX (US); Shanrong Zhang, Dallas, TX (US); Kuangcong Wu, Plano, TX (US)

(73) Assignee: Board of Regents The University of Texas System, Austin, TX (US)

( * ) Notice: Subject to any disclaimer, the term of this patent is extended or adjusted under 35 U.S.C. 154(b) by 113 days.

(21) Appl. No.: 10/001,858

(22) Filed: Nov. 20, 2001

(65) Prior Publication Data

US 2002/0127182 A1 Sep. 12, 2002

Related U.S. Application Data

(60) Provisional application No. 60/252,269, filed on Nov. 20, 2000.

(51) Int. Cl.$^7$ .............................................. A61B 5/055

(52) U.S. Cl. ...................... 424/9.363; 424/9.1; 424/9.3; 424/9.361; 424/9.36; 540/145

(58) Field of Search .................... 534/10–16; 424/1.11, 424/1.65, 9.1, 9.3, 9.32, 9.36, 9.362, 9.33; 540/450, 145

(56) References Cited

U.S. PATENT DOCUMENTS

| | | | |
|---|---|---|---|
| 5,050,609 | A | 9/1991 | Balaban |
| 5,712,389 | A | 1/1998 | Meyer et al. |
| 5,914,095 | A | 6/1999 | Watson |
| 5,919,432 | A | 7/1999 | Meyer et al. |
| 6,143,274 | A | 11/2000 | Tweedle et al. |
| 6,149,890 | A | 11/2000 | Uggeri et al. |
| 6,177,562 | B1 | 1/2001 | Uggeri et al. |
| 2002/0127182 | A1 * | 9/2002 | Sherry et al. ............ 424/9.363 |

FOREIGN PATENT DOCUMENTS

| | | |
|---|---|---|
| WO | WO 91/03200 | 3/1991 |
| WO | WO 93/12097 | 6/1993 |
| WO | WO 00/47111 | 8/2000 |
| WO | WO 0066180 | 11/2000 |

OTHER PUBLICATIONS

Aime et al (199), Chem. Commun., pp. 1047–1048.*
Shanrong Zhang, Kuangcong Wu, Michael C. Biewer, and A. Dean Sherry, 1H and 17O NMR Detection of a Lanthanide–Bound Water Molecule at Ambient Temperatures in Pure Water as Solvent, 2001 American Chemical Society, Inorganic Chemistry, Nov. 17, 2001, vol.40, p. 4284–4290.
Shanrong Zhang, Kuangcong Wu, and A. Dean Sherry, A Novel pH–Sensitive MRI Contrast Agent, Angew. Chem. Int. Ed., 1999, 38, No. 21, p. 3192–3194.

Andrei S. Batsanov, Andrew Bebby, James I. Bruce, Judith A. K. Howard, Alan M. Kenwright and David Parker, Direct NMR and luminescence observation of water exchange at cationic ytterbium and europium centres, Chem. Commun., 1999, p. 1011–1012.
Silvio Aime, Mauro Botta, James I. Bruce, Valentina Mainero, David Parker and Enzo Terreno, Modulation of the water exchange rates in [Gd–DO3A] complex by formation of ternary complexes with carboxylate ligands. The Royal Society of Chemistry, 2001, p. 115–116.
Shanrong Zhang, Zoltan Kovacs, Shawn Burgess, Silvio Aime, Enzo Terreno, and A. Dean Sherry, {DOTA–bis(amide)} lanthanide Complexes: NMR Evidence for Differences in Water–Molecule Exchange Rates for Coordination Isomers, Chem. Eur. J., 2001, 7, No. 1, p. 288–296.
Peter Caravan, Jeffrey J. Ellison, Thomas J. McMurray, and Randall B. Lauffer, Gadolinium (III) Chelates as MRI Contrast Agents: Structure, Dynamics, and Applications, American Chemistry Society, Chemical Reviews, 1999, 99, p. 2293–2352.
Lucia Alderighi, Antonio Bianchi, Luisella Calabi, Paolo Dapporto, Claudia Giorgi Pietro Losi, Lino Paleari, Paolo Paoli, Patrizia Rossi, Barbara Valtancoli, and Mario Virtuani, Solution Study, Crystal Structure and Relaxivity Properties of a Gd3 + Complex with an Uncharged Macrocyclic Ligand Bearing Four Amidic Side Arms, Eur. J. Inorg. Chem, 1998, p. 1581–1584.
Silvio Aime, Alessandro Barge, Mauro Botta, Alvaro S. De Sousa, and David Parker, Direct NMR Spectroscopic Observation of a Lanthanide–Coordinated Water Molecule whose Exchange Rate is Dependent on the Conformation of the Complexes, Angew. Chem. Int. Ed., 1998 37, No. 19, p. 2673–2675.
K. M. Ward, A. H. Aletras, and R. S. Balaban, A New Class of Contrast Agents for MRI Based on Proton Chemical Exchange Dependent Saturation Transfer (CEST), Journal of Magnetic Resonance, 2000, 143, p. 79–87.

(Continued)

Primary Examiner—Dameron L. Jones

(57) ABSTRACT

The present invention is directed, in general, to contrast agents (CA), and methods and systems of using such agents for producing image contrast based on a magnetization transfer (MT) mechanism. The CA comprises a tetraazacyclododecane ligand having pendent arms R, R', R" and R'" that are amides having a general formula: —CR$_1$H—CO—NH—CH$_2$—R$_2$. R$_1$ includes organic substituents and R$_2$ is not hydrogen. A paramagnetic metal ion (M) is coordinated to the ligand. The method, comprises subjecting a CA, in a sample, to a radio frequency pulse. The CA has pendent arms R, R', R" and R'" comprising organic substituents and the ligand further includes a M and a water molecule. A signal is obtained by applying a radio frequency pulse at a resonance frequency of the water molecule. The magnetic resonance system, comprises a magnetic resonance apparatus and the CA, the agent containing a ligand having the above described general formula.

23 Claims, 30 Drawing Sheets

OTHER PUBLICATIONS

Silvio Aime, Alessandro Barge, Mauro Botta, David Parker, and Alvaro S. De Sousa, Prototropic vs Whole Water Exchange Contributions to the Solvent Relaxation Enhancement in the Aqueous Solution of a Cationic Gd3+ Macrocyclic Complex, American Chemistry Society, 1997, 119, p. 4767–4768.

Silvio Aime, Alessandro Barge, James I. Bruce, Mauro Botta, Judith A. K. Howard, Janet M. Maloney, David Parker, Alvaro S. De Sousa, and Mark Woods, NMR, Relaxometric, and Structural Studies of the Hydration and Exchange Dynamics of Cationic Lanthanide Complexes of Macrocyclic Tetramide Ligands, American Chemistry Society, 1999, 121, p. 5762–5771.

Frank A. Dunand, Silvio Aime, and Andre E. Merbach, First 170 NMR Observation of Coordinated Water on Both Isomers of [Eu(DOTAM)(H20)]3+: A Direct Access to Water Exchange and its Role in the Isomerization, American Chemical Society, 2000, 122, p. 1506–1512.

Shanrong Zhang, Patrick Winter, Kuangcong Wu, and A. Dean Sherry, A Novel Europium (III)–Based MRI Contrast Agent, American Chemistry Society, 2001, 123, p. 1517–1518.

Nicholas Goffeney, Jeff W. M. Bulte, Jeff Duyn, L. Henry Bryant Jr., and Peter C. M. Van Zijl, Sensitive NMR Detection of Cationic–Polymer–Based Gene Delivery Systems Using Saturation Transfer via Proton Exchange, American Chemistry Society, 2001, 123, p. 8628–8629.

V. Guivel–Scharen, T. Sinnwell, S. D. Wolff, and R. S. Balaban, Detection of Proton Chemical Exchange between Metabolites and Water in Biological Tissues, Journal of Magnetic Resonance, 1998, 133, p. 36–45.

Shanrong Zhang, Huangcong Wu, and A. Dean Sherry, Gd3+ Complexes with Slowly Exchanging Bound–Water Molecules May Offer Advantages in the Design of Responsive MR Agents, Investigative Radiology, 2001, vol. 36, No. 2, p. 82–86.

R. M. Hengelman, G. J. Stanisz and S. J. Graham, Magnetization transfer in MRI: a review, NMR Biomed, 2001, 14, p. 57–64.

K. M. Ward and R. S. Balaban, Determination of pH Using Water Protons and Chemical Exchange Dependent Saturation Transfer (CEST), Magnetic Resonance in Medicine, 2000, 44, p. 799–802.

Zhang, et al.; "A Novel pH Sensitive MRI Contrast Agent"; Angew. Chemical International Edition 1999; vol. 38; No. 21, pp. 3192–3194.

Tanttu, et al.; "Synergistic Enhancement of MRI with Gd–DTPA and Magnetization Transfer"; Journal of Computer Assisted Tomography; vol. 16, No. 1; 1992; pp. 19–24.

Jones et al.; "Improving the Contrast in Rapid Imaging Sequences With Pulsed Magnetization Transfer Contrast"; Journal of Magnetic Resonance; 1992; vol. 97, No. 1; pp. 171–176.

Balaban et al.; "Magnetization Transfer Contrast in Magnetic Resonance Imaging"; Magnetic Resonance Quarterly, vol. 8, No. 2, 1992; pp. 116–137.

Zhang et al.; "A Novel Europium (III) Based MRI Contract Agent"; 2001 American Chemical Society; vol. 123, No. 7; p. 1518.

Zhang et al.; "DOTA–Bis (Amide)Lanthanide Complexes: NMR Evidence for Differences in Water–Molecule Exchange Rates for Coordination Isomers", Chem. Eur. J. 2001, vol. 7, No. 1; pp. 288–296.

Aime et al.; "Paramagnetic Lanthanide(III) Complexes as pH–Sensitive Chemical Exchange Saturation Transfer (CEST) Contrast Agents for MRI Applications", Magnetic Resonance in Medicine, vol. 47, No. 4, Apr. 2002; pp. 639–648.

Zhang et al.; "Unusually Sharp Dependence of Water Exchange Rate Versus Lanthanide Ionic Radii for a Series of Tetramide Complexes"; Journal American Society, 2002, vol. 124, No. 16; pp. 4226–4227.

* cited by examiner

No Saturation
(no sat)

Saturation at -6400 Hz
(Satp)

Saturation at +6400 Hz
(Satn)

Difference Image
(no sat - Satp)

Difference Image
(Satn - Satp)

No Saturation (no sat)     Saturation at +11500 Hz (Satp)     Saturation at -115800 Hz (Satn)

Difference Image (no sat - Satp)     Difference Image (Satn - Satp)

a) Satfrq = +11500Hz

Satpl=0   5   10   20   30   40   50   60 b) Satfrq = -11500Hz c) Difference Images a) Satfrq = -1200Hz b) Satfrq = +1200Hz c) Difference Images

PARAMAGNETIC METAL ION-BASED MACROCYCLIC MAGNETIZATION TRANSFER CONTRAST AGENTS AND METHOD OF USE

CROSS-REFERENCE TO PROVISIONAL APPLICATION

This application claims the benefit of U.S. Provisional Application 60/252,269, filed Nov. 20, 2000.

TECHNICAL FIELD OF THE INVENTION

The present invention is directed to contrast agents and methods of using contrast agents for altering the magnetic resonance signal of samples, and more particularly, to paramagnetic metal ion-macrocylic complexes as contrast agents and methods of using such agents for producing image contrast based on a magnetization transfer mechanism.

BACKGROUND OF THE INVENTION

Contrast agents (CAs) are widely used to enhance magnetic resonance imaging (MRI) contrast. The administration of Extrinsic CAs, such as gadolinium (Gd) containing CAs, are thought to achieve contrast by the paramagnetic relaxation effect of a metal-ion to shorten the bulk water relaxation time via rapid exchange of the metal ion's inner-sphere water molecules with bulk solvent. The ability to turn CAs on or off raises the possibility of using such CAs to measure changes in physiological status of tissue samples. For example some CAs exclude Gd from the inner sphere while inactive, and then on activation expose bulk water to a rapidly exchanging water site on the Gd. However, the utility of such CAs in living subjects may be limited by toxicity and undesirable spin-spin lattice relaxation time (T2*) effects. In addition, CAs having a slow rate of water exchange are disfavored because this hampers the metal-ion's ability to shorten the bulk water relaxation time and thus enhance contrast.

Chemical exchange saturation transfer (CEST) is an alternative technique to enhance MRI contrast. Contrary to the above described CAs, CEST favors CAs having a slow rate of water exchange. For example, intrinsic metabolites with slowly exchangeable NH or OH sites may be saturated to produce a direct intensity decrease in the bulk water signal by Magnetization Transfer (MT). It may also be possible to develop MT-based CA that turn on an off in response to a physiologic parameter, such as pH, if the exchange rate of the NH or OH sites are sensitive to changes in that parameter. However, because the chemical shifts of such diamagnetic NH and OH groups in intrinsic metabolites are typically within 5 ppm of bulk water, it can be difficult to avoid off-resonance saturation of bulk water or tightly protein-bound water in tissue samples. Extrinsic CAs may similarly enhance image contrast by MT. Such CAs, however, rely on the chemical exchange of NH or OH functional groups covalently bonded to the CA and close to the resonance frequency of bulk water.

Accordingly, what is needed is an improved MT-based CA that is amenable to discriminating and reporting on the changing metabolic status of a target sample in contrast to its surroundings.

SUMMARY OF THE INVENTION

To address the deficiencies of the prior art, the present invention, in one embodiment, provides a contrast agent comprising: a tetraazacyclododecane ligand having a general formula as follows:

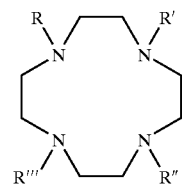

wherein pendent arms R, R', R" and R'" are amides having a general formula: —CR$_1$H—CO—NH—CH$_2$—R$_2$, wherein R$_1$ includes organic substituents and R$_2$ is not hydrogen; and a paramagnetic metal ion coordinated to the tetraazacyclododecane ligand.

In another embodiment, the present invention provides a method of using a magnetic resonance (MR) contrast agent, comprising: subjecting a contrast agent contained within a sample to a radio frequency pulse wherein the contrast agent is a tetraazacyclododecane ligand having the above described general formula, wherein pendent arms R, R', R" and R'" comprise organic substituents and the tetraazacyclododecane ligand further includes a paramagnetic metal ion coordinated to the tetraazacyclododecane ligand and a water molecule associated with the tetraazacyclododecane ligand; and obtaining a magnetization transfer signal by applying a radio frequency pulse at a resonance frequency of the water molecule.

Yet another embodiment provides a magnetic resonance system, comprising: a magnetic resonance (MR) contrast agent, wherein the MR agent tetraazacyclododecane ligand has the above described general formula, wherein pendent arms R, R', R" and R'" comprise organic substituents and the tetraazacyclododecane ligand further includes a paramagnetic metal ion coordinated to the tetraazacyclododecane ligand and a water molecule associated with the tetraazacyclododecane ligand, wherein the MR contrast agent produces a magnetization transfer signal when subjected to a radio frequency pulse; and a magnetic resonance apparatus.

The foregoing has outlined, preferred and alternative features of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention. Those skilled in the art should also realize that such equivalent constructions do not depart from the spirit and scope of the invention.

BRIEF DESCRIPTION OF THE DRAWINGS

For a more complete understanding of the invention, reference is now made to the following descriptions taken in conjunction with the accompanying drawing, in which.

DETAILED DESCRIPTION

Figure 1:
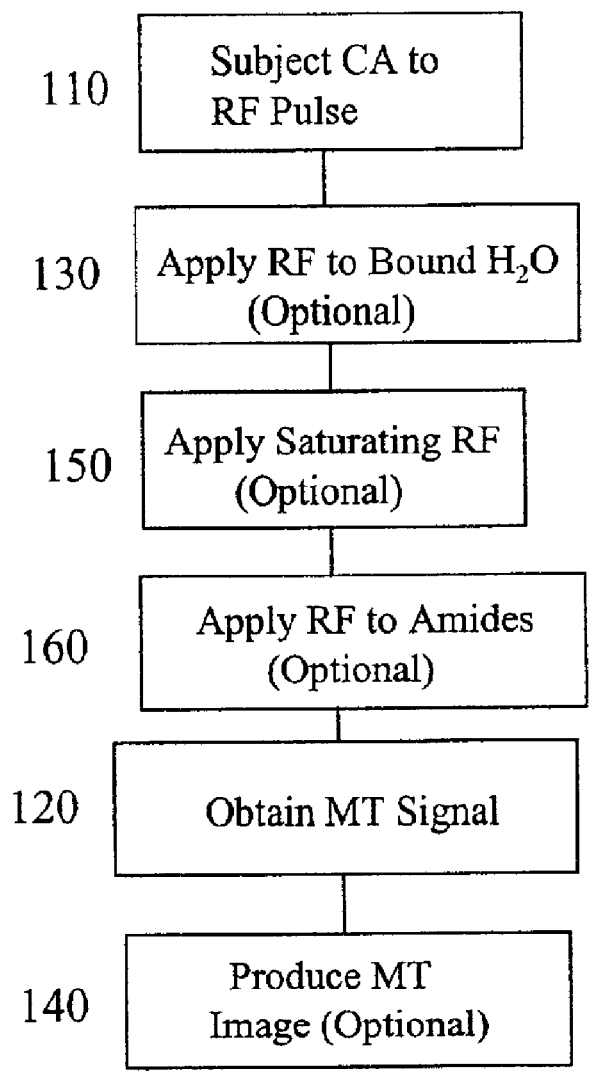
FIG. 1 illustrates a method of using a magnetic resonance contrast agent according to the present invention.

It has been found that water exchange rates for water molecules bound to certain paramagnetic metal ion-macrocylic complexes were sufficiently slow that a separate bound water MR signal, substantially up field or downfield (e.g., about $\pm 6$ ppm or more) from the bulk water MR signal, is observable at room temperature in pure water as solvent. Furthermore, this highly shifted and slowly exchanging bound water molecule may be irradiated to produce magnetization transfer (MT) on bulk water and thereby serve as an effective CA.

The theory of MT had been known for several decades and was widely used in chemistry and biology. See e.g., Forsen S. & Hoffman R. A., 39 J.Chem.Phys. 2892 (1963) and 40 J.Chem.Phys. 1189 (1964); Dwek, R. A. Nuclear Magnetic Resonance (N.M.R.) In Biochemistry (Oxford University Press, London, 1973); incorporated herein by reference.

Theoretically, the extent of observed MT depends on chemical exchange and relaxation:

$$\frac{M_{on}}{M_{off}} = \left(\frac{1}{1+k_{obs}T_{1sat}}\right) + \left(\frac{k_{obs}T_{1sat}}{1+k_{obs}T_{1sat}}\right)\exp\left[-\frac{(1+k_{obs}T_{1sat})}{T_{1sat}} \times t\right] \quad (1)$$

where $M_{on}$ and $M_{off}$ represent the bulk water signal intensity with or without selective Radio Frequency (RF) irradiation at the exchanging sites, respectively. $k_{obs}$ is the pseudo-first order exchange rate between bulk water and the exchanging protons, given by the concentration ratio of the exchanging sites relative to water protons divided by the lifetime of the exchange sites, $\tau_M$. $T_{1sat}$ is the spin-lattice relaxation time of the bulk water protons during saturation of the exchangeable protons. For paramagnetic systems, $T_{1sat}$ is no longer a constant, but is rather described by standard theory of paramagnetic relaxation, summarized in equation (2):

$$\frac{1}{T_{1sat}} = r_1[CA] + \frac{1}{T_{1dia}} \quad (2)$$

Here $r_1$ is the relaxivity ($mM^{-1}s^{-1}$) of the CA, originating from both inner- and outer-sphere paramagnetic contributions. See e.g., Lauffer R. B., 87 Chem.Rev. 901 (1987), incorporated herein by reference.

To observe a MT effect, the system ideally should be in an exchange limiting regime, defined as $\Delta\omega \cdot \tau_M \geq 1$. The difference in frequency between the MR frequency of the exchanging sites and the MR frequency of bulk water is defined as $\Delta\omega$. The life-time of the exchanging site is defined as $\tau_M$. One advantage of certain paramagnetic lanthanide macrocylic complexes of the present invention displaying a large $\Delta\omega$ is that faster exchange may take place, because $\tau_M$ is short, without approaching the exchange limit. Moreover, because the resonance frequency of the exchangeable water molecule site is distant from bulk water. For example, $\Delta\omega$ corresponds to about ±6 ppm to about ±500 ppm, and preferably about ±16 ppm to ±500 ppm. It is therefore possible to saturate the exchanging site while minimizing off-resonance saturation (i.e., direct saturation) of bulk water, and resulting non-specific, detrimental decreased MR signal intensity.

The CA of the present invention includes a tetraazacyclododecane ligand having a general formula as follows:

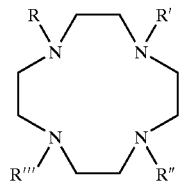

The pendent arms R, R', R" and R'" are amides having a general formula: —CR₁H—CO—NH—CH₂—R₂, $R_1$ includes organic substituents and $R_2$ is not hydrogen.

The CA may further include a water molecule, referred to as a bound water molecule, as the exchanging group. The bound water molecule is associated with the tetraazacyclododecane ligand and paramagnetic metal ion such that the bound water molecule has a $\Delta\omega \cdot \tau_M \geq 1$. In certain advantageous embodiments of the CA, the bound water has a $\Delta\omega \geq 6$ ppm. In other embodiments of the CA, the bound water molecule has the $\tau_M \geq 1$ μs.

The CA further comprises a paramagnetic metal ion coordinated to the tetraazacyclododecane ligand. Any paramagnetic metal ion is within the scope of the lanthanide invention, although certain metal ions of the lanthanide group are preferred. As further detailed in the Experiments below, at magnetic field strengths below 4.7 Tesla (T) the preferred metal ion includes one of $Eu^{3+}$, $Tb^{3+}$, $Dy^{3+}$ or $Ho^{3+}$. At higher field strengths the metal ion may also include $Pr^{3+}$, $Nd^{3+}$, $Sm^{3+}$, $Er^{3+}$ or $Tm^{3+}$.

In certain preferred embodiments of this CA, $R_2$ does not have a proton exchangeable group and is not hydrogen. In other preferred embodiments, $R_2$ may comprise alkyl groups having 20 carbon atoms or less, cycloalkyl groups having 20 carbon atoms or less, alkyloxy groups having 20 carbon atoms or less, alkyl ethers having 10 oxygen atoms or less and 20 carbon atoms or less, or polyols having 20 carbon atoms or less. $R_1$ may comprise H, alkyl groups having 20 carbon atoms or less, cycloalkyl groups having 20 carbon atoms or less, alkyloxy groups having 20 carbon atoms or less, alkyl ethers having 10 oxygen atoms or less and 20 carbon atoms or less, or polyols having 20 carbon atoms or less.

Another embodiment of the present invention is a method 100 of using a magnetic resonance (MR) contrast agent. As illustrated in FIG. 1, the method comprises subjecting 110 a contrast agent contained within a sample to a radio frequency (RF) pulse. Here, the contrast agent (CA) is a tetraazacyclododecane ligand having the general formula as presented below:

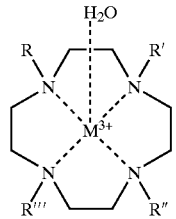

where pendent arms R, R', R" and R'" comprise organic substituents and the tetraazacyclododecane ligand further includes a paramagnetic metal ion ($M^{3+}$) coordinated to the tetraazacyclododecane ligand and a water molecule (bound $H_2O$) associated with the tetraazacyclododecane ligand. The method 100 further comprises obtaining 120 a magnetization transfer (MT) signal by applying 130 a radio frequency pulse at a resonance frequency of the water molecule. In a preferred embodiment of method 100 the water molecule, referred to as a bound water molecule, has a $\Delta\omega \cdot \tau_M \geq 1$. optionally, method 100 may further include producing a magnetization transfer MR image 140 from the magnetization transfer signal. Method 100 may optionally further include applying a saturating pulse radio 150 frequency pulse to produce the magnetization transfer signal. Those skilled in the art, however, understand that other means of producing magnetization transfer, for example applying a frequency specific 180° pulse or multi-dimensional NMR techniques, are within the scope of the present invention.

In one embodiment of method 100 the CA has at least one, and preferably four, pendent arms containing an amide group. Such embodiments of method 100 include obtaining the magnetization transfer signal 120 by applying a radio frequency pulse 160 at a resonance frequency of the protons associated with the amide. As further demonstrated in the Experiments below, the radio frequency pulse may be applied at the resonance frequency of one or all of the exchangeable protons associated with the amide to produce a magnetization transfer signal that is sensitive to pH. The relationship between pH and the magnetization signal may be further be preferably expressed as a ratio of the MT signal obtained while applying the radio frequency pulse one exchangeable amide proton relative to the MT signal obtained while applying the radio frequency pulse to a second or all of the exchangeable amide protons.

In certain preferred embodiments of method 100, where the pendent arms of the CA each contain an amide group, the pendent arms are identical and have the general formula: —$CHR_1$—CO—$NR_2$—$R_3$, wherein $R_1$, $R_2$ and $R_3$ comprise organic substituents. In one preferred embodiment of this type of CA, the $R_1$ and $R_2$ are H, and the $R_3$ has the general formula: —$(CH_2)_n COOR_4$ where n=1–20, and the $R_4$ is H, a Group IA or IIA metal ions or alkyl group containing from one to twenty carbon atoms. In these preferred embodiments, the paramagnetic metal ion is preferably $Tb^{3+}$, $Dy^{3+}$ or $Ho^{3+}$ at magnetic field strengths less than 4.7 T, or additionally, $Eu^{3+}$, $Pr^{3+}$ or $Nd^{3+}$ at higher magnetic field strengths (i.e., 4.7 to 11.75 T). In a second preferred embodiment of the above-described CA, the $R_1$ and $R_2$ are H, and the $R_3$ has the general formula: —$(CH_2)_n P(O)(OR_4 OR_5)$ where n=1–20; $R_4$ is H, an alkaline earth metal ion of Groups IA or IIA or an alkyl group containing one to twenty carbon atoms; and $R_5$ also is H, an alkaline earth metal ion of Groups IA or IIA or an alkyl group containing one to twenty carbon atoms. In a third preferred embodiment of the above-described CA, the $R_1$ and $R_2$ may be H, and the $R_3$ has the general formula: —$(CH_2)_n R_4$ where n=1–20; and $R_4$ is Pyridine (Py) or Phenol (Ph).

In another embodiment of method 100, the CA has pendent arms R and R" that are identical, the pendent arms R' and R'" are identical, and the pendent arms R' and R'" are not equal to the pendent arms R and R". In one preferred embodiment of the above-described CA, the pendent arms R and R" have the general formula: —$CHR_1$—CO—NH—$R_2$; and the pendent arms R' and R'" have the general formula: —$CHR_3$—CO—NH—$R_4$ where $R_1$, $R_2$, $R_3$, and $R_4$ comprise organic substituents, and the $R_2$ is not equal to the $R_4$.

Figure 2:
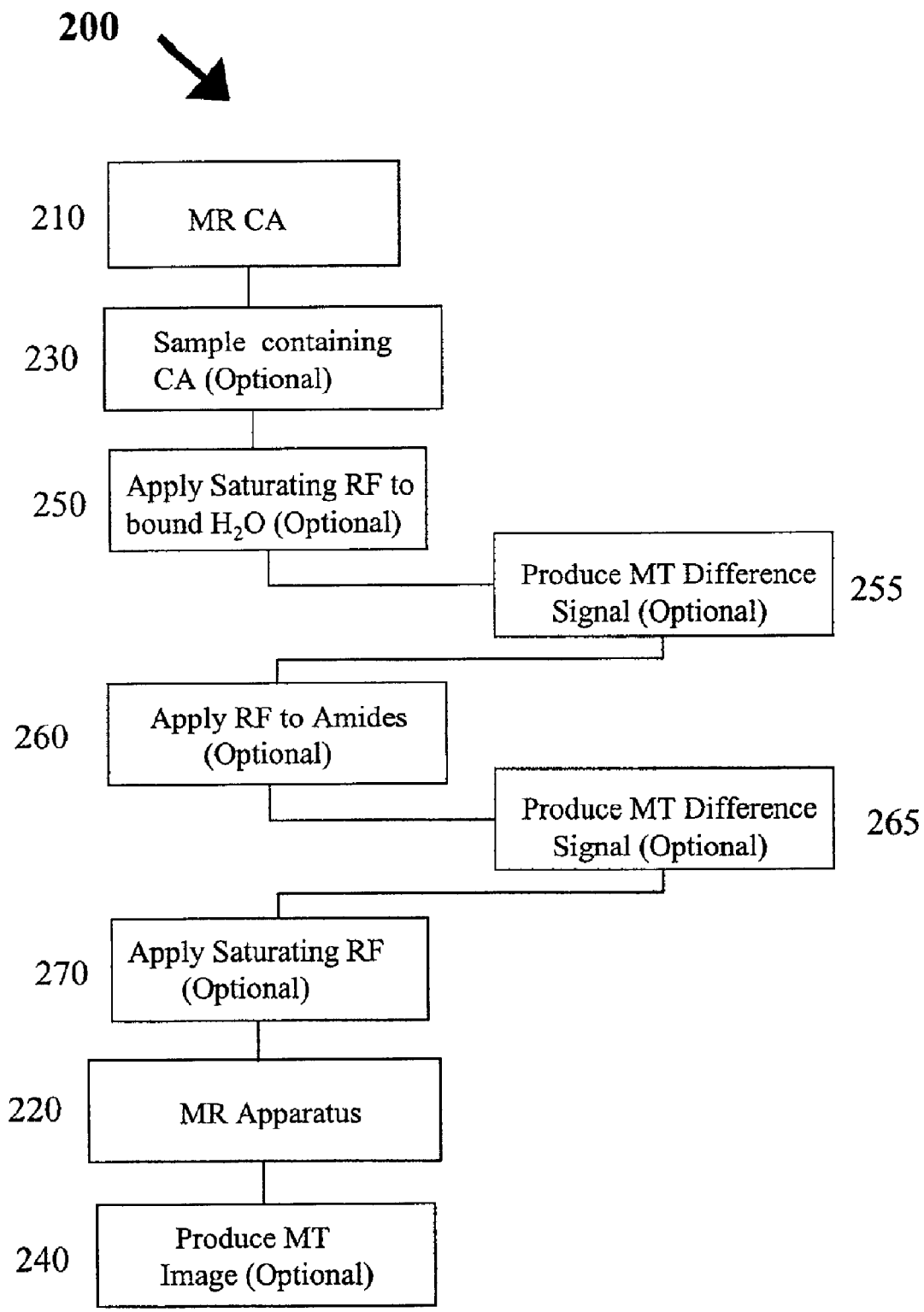
FIG. 2 illustrates a magnetic resonance system according to the present invention.

Yet another embodiment of the present invention is a magnetic resonance system 200. As illustrated in FIG. 2, the system 200 comprises a magnetic resonance (MR) contrast agent (CA) 210, wherein the MR agent contains a tetraazacyclododecane ligand having the same general formula described for method 100. The CA 210 includes pendent arms R, R', R" and R'" that comprise organic substituents. CA 210 further includes a paramagnetic metal ion coordinated to a water molecule, referred to as a bound water molecule, associated with the tetraazacyclododecane ligand, where the MR contrast agent produces a magnetization transfer signal when subjected to a radio frequency pulse. In certain embodiments of the present invention, the CA includes at least one and up to twenty tetraazacyclododecane ligands. Such ligands may be covalently or noncovalently bonded to a carrier, such as a protein or polymer, comprising a portion of the CA. Collecting several such ligands, and associated metal ions and bound water molecules, allows effective MT contrast to be achieved at lower concentrations of CA. The system 200 further comprises a magnetic resonance apparatus 220. One of ordinary skill in the art understands that the MR apparatus may include all the hardware and software components necessary to produce magnetic resonance spectra or images.

The system 200 may further comprise a sample 230 that contains the CA 220 within it. The sample includes living subject including animal, for example human, species, or a portion of fluid or tissue withdrawn from the subject. Alternatively, the sample 230 containing the CA 220 may be an inanimate object, or contain other non-living material. In one preferred embodiment of the MR system 200, the magnetic resonance apparatus 210 produces a magnetization transfer image 240 of the sample 230 from the magnetization transfer signal. Such a system 200 may preferably produce the image by applying the radio frequency pulse at a resonance frequency of the bound water molecule 250. Alternatively the radio frequency signal may be applied at the resonance frequency of protons associated with an amide included in one or more of the pendent arms of the CA 260.

In certain preferred embodiments of the MR system 200, the magnetic resonance apparatus produces a magnetization transfer difference signal 255 by applying the radio frequency pulse at a $\Delta\omega$ of the bound water molecule, acquiring the magnetization transfer signal and subtracting the signal from a MR signal obtained by applying a radio frequency pulse at $-\Delta\omega$. A difference signal may be produced in analogous fashion, by applying the radio frequency pulse at a $\Delta\omega$ of the protons associated with amides 265 in the pendent arms of the CA 210 and subtracting the signal from a MR signal obtained by applying a radio frequency pulse at $-\Delta\omega$. In certain embodiments either difference signals 255, 265 may be further processed by the apparatus 220 to produce a difference image. The magnetic resonance system 200 may further include in the apparatus 220 hardware that produces a saturating pulse 270. The saturating pulse is preferably sufficiently frequency specific to saturate only the exchangeable protons, for example the bound water or the protons associated with the amides contained within the pendent arms of the CA 210. The saturating pulse preferably ranges from about 1 to about 3 seconds.

The CA 210 used in the MR system 200 may include any of the embodiments of CA discussed above in the method 100. However, the exchangeable proton within the CA 210, for example bound water, preferably has a $\Delta\omega \cdot \tau_M \geq 1$. In certain embodiments of the MR system 200, the $\Delta\omega \geq 6$ ppm. In other preferred embodiments of the MR system 200, the $\tau_M \geq 1$ μs.

Experiments

Examples of CAs prepared according to the present invention are presented below for illustrative purposes and do not limit the scope of the claimed invention. The synthesis of polyazamacrocyles having pendent arms comprising organic substitutants has been described in: U.S. Pat. No. 5,428,155, to Sherry A. D. and van Westrenen, J.; Kovacs and Sherry, *pH-Controlled Selective Protection of Polyaza Macrocycles*, Synthesis, 761–63, (July 1997); Zhang S., Winter P., Wu. K. & Sherry A. D., *A Novel Europium(III)-Based Contrast Agent*, 123 J.Am.Chem.Soc. 1517–18 (2001); Zhang S., Wu. K., Biewer M. C., & Sherry A. D. $^1H$ and $^{17}O$ *NMR Detection of a Lanthanide-Bound Water Molecule at Ambient Temperatures in Pure Water*, 40 Inorg. Chem. 4284–90 (2001); which are incorporated herein by reference.

Experiment 1

A first experiment, examined the life times at 298° K; $\tau_M^{298}$, of water molecules bound to various lanthanide-macrocylic complexes of the present invention, and having the general formula, $Ln(1)^{3+}$, where the four pendent arms R, R', R" and R'" are all ethyl-acetamidoacetate (i.e., LnDOTA-4AmCE$^{3+}$), as depicted below:

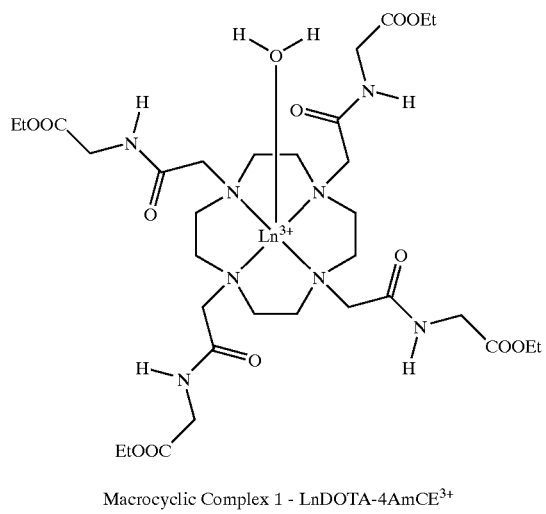

Macrocyclic Complex 1 - LnDOTA-4AmCE$^{3+}$

Figure 3:
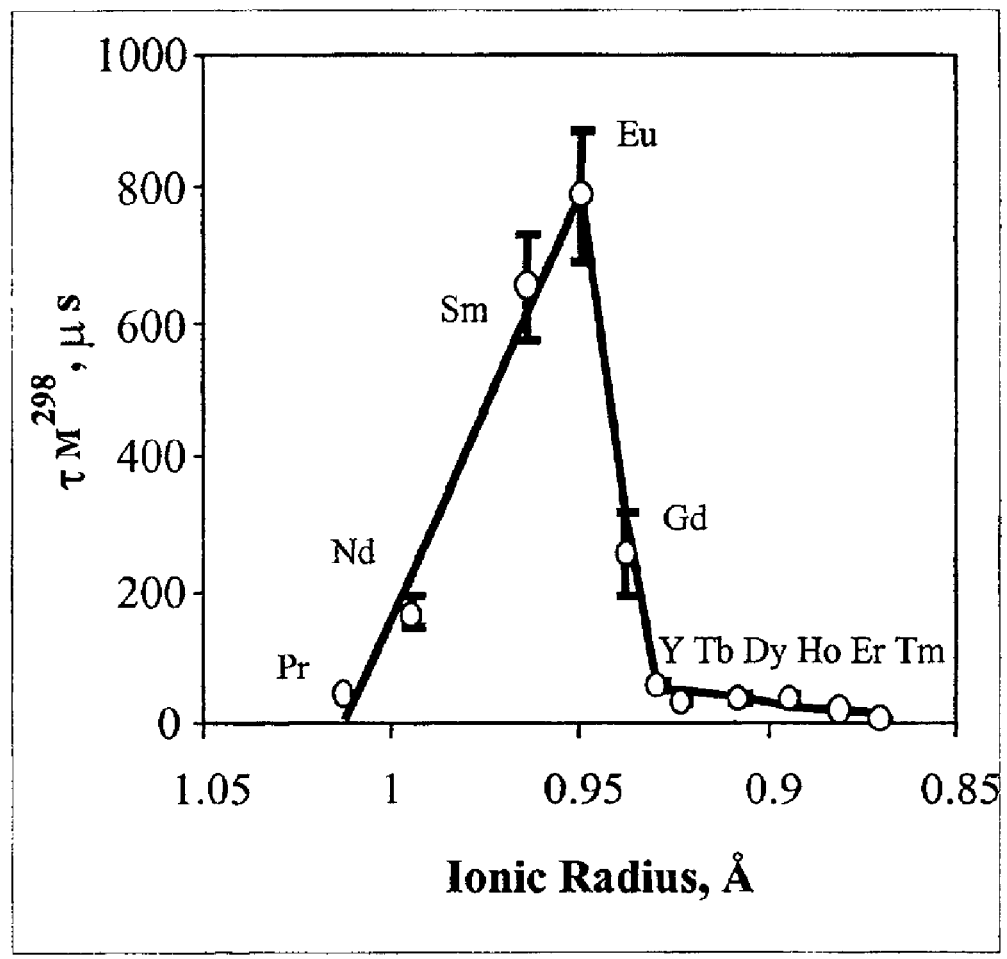
FIG. 3 illustrates the dependence of $\tau_M^{298}$ on the radius of the central lanthanide ion for a series of lanthanide ion (Ln$^{3+}$) complexes of the present invention.

As illustrated in FIG. 3, $\tau_M^{298}$ is strongly dependent on the radius of the central lanthanide ion. The plot shows the $\tau_M^{298}$ measured for a series of Ln(1)$^{3+}$ complexes in acetonitrile plus 2–4% water versus the Ln$^{3+}$ ionic radii. Individual $\tau_M^{298}$ values were obtained by fitting the temperature dependent $^{17}$O NMR bound water line widths according to standard exchange theory. In a separate series of experiments, it was found that $\tau_M^{298}$ was about 2-fold shorter when pure water was the solvent. Because the bulk water $^{17}$O resonance of Yb(1) solution was relatively narrow at all temperatures, no attempt was made to determine $\tau_M^{298}$ for this complex based on the $^{17}$O NMR line width data from bulk water. However, a fit to the bound-water $^1$H NMR line width gave a $\tau_M^{298}$ of 5.8 µs for Yb(1), consistent with the trend shown in FIG. 3. Moreover, $^1$H NMR line width fitting gave very similar results for those systems for which the bound water is directly observable.

As further illustrated in Table 1, the proton chemical shifts of bound water in these lanthanide-macrocylic complexes, δ, relative to bulk water, at 0 ppm are generally highly shifted, either more than 6 ppm downfield or upfield (i.e., ±6 ppm or more), depending upon the properties of the central lanthanide ions. The exchange limit regime, $\Delta\omega\cdot\tau_M$, calculated for different field strengths is also shown in Table 1. At 1.5 Tesla (T), a magnetic field strength presently used by many commercial MRI scanners, the exchange limit regimes, $\Delta\omega\cdot\tau_M$, of Eu(1)$^{3+}$, Tb(1)$^{3+}$, Dy(1)$^{3+}$, and Ho(1)$^{3+}$ are all greater than 1. At higher fields, however, such as 4.7 T and 11.75 T, more lanthanide complexes have exchange limit regimes greater than 1, with $\Delta\omega\cdot\tau_M$ increasing as field strength increases. Therefore, favorable MT contrast effects are available for a broad range of lanthanide-macrocylic complexes over a broad range of magnetic field strengths.

TABLE 1

| Ln(1)$^{3+}$ Complexes | Observation of bound water | $\tau_M$ (µs) | δ (ppm) | $\Delta\omega\cdot\tau_M$ 11.75 T | 4.7 T | 1.5 T |
|---|---|---|---|---|---|---|
| Pr$^{3+}$ | Yes | 20 | −60 | 3.8 | 1.5 | 0.5 |
| Nd$^{3+}$ | Yes | 80 | −32 | 8.0 | 3.2 | 1.0 |
| Sm$^{3+}$ | Yes | 320 | −4 | 4.0 | 1.6 | 0.5 |
| Eu$^{3+}$ | Yes | 382 | 50 | 60.0 | 24.0 | 7.7 |
| Tb$^{3+}$ | No | 31 | −600 | 58.5 | 23.4 | 7.5 |

TABLE 1-continued

| Ln(1)$^{3+}$ Complexes | Observation of bound water | $\tau_M$ (µs) | δ (ppm) | $\Delta\omega\cdot\tau_M$ 11.75 T | 4.7 T | 1.5 T |
|---|---|---|---|---|---|---|
| Dy$^{3+}$ | No | 17 | −720 | 38.5 | 15.4 | 4.9 |
| Ho$^{3+}$ | No | 19 | −360 | 21.5 | 8.6 | 2.8 |
| Er$^{3+}$ | No | 9 | 200 | 5.7 | 2.3 | 0.7 |
| Tm$^{3+}$ | Yes | 3 | 500 | 4.7 | 1.9 | 0.6 |
| Yb$^{3+}$ | Yes | 3 | 200 | 1.9 | 0.5 | 0.2 |

Experiment 2

Figure 4:
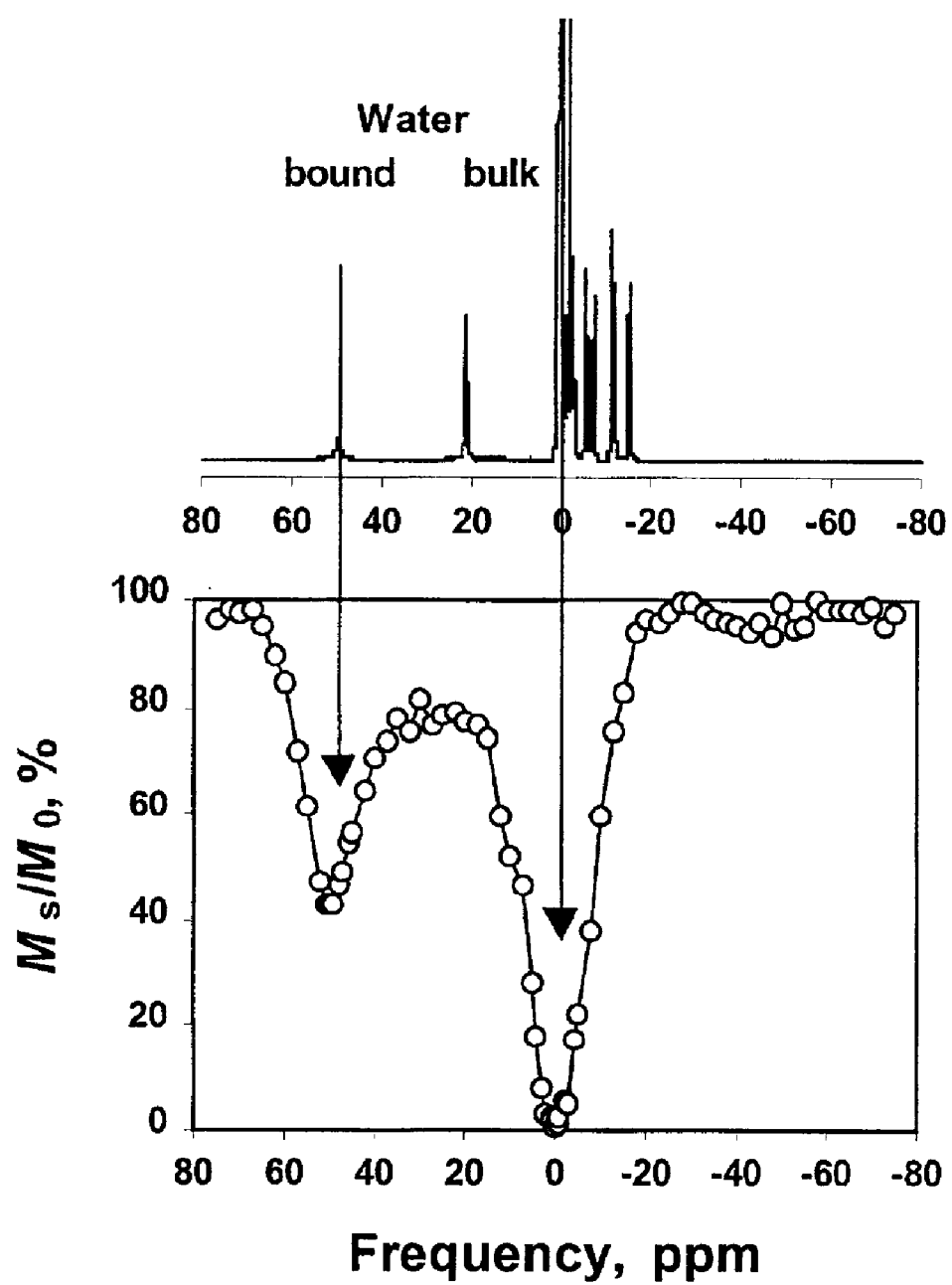
FIG. 4 illustrates an exemplary $^1$H NMR spectrum of the Eu(1)$^{3+}$ complex produced according to the present invention in the absence of a saturating pulse, and a MT profile for the complex.
Figure 5:
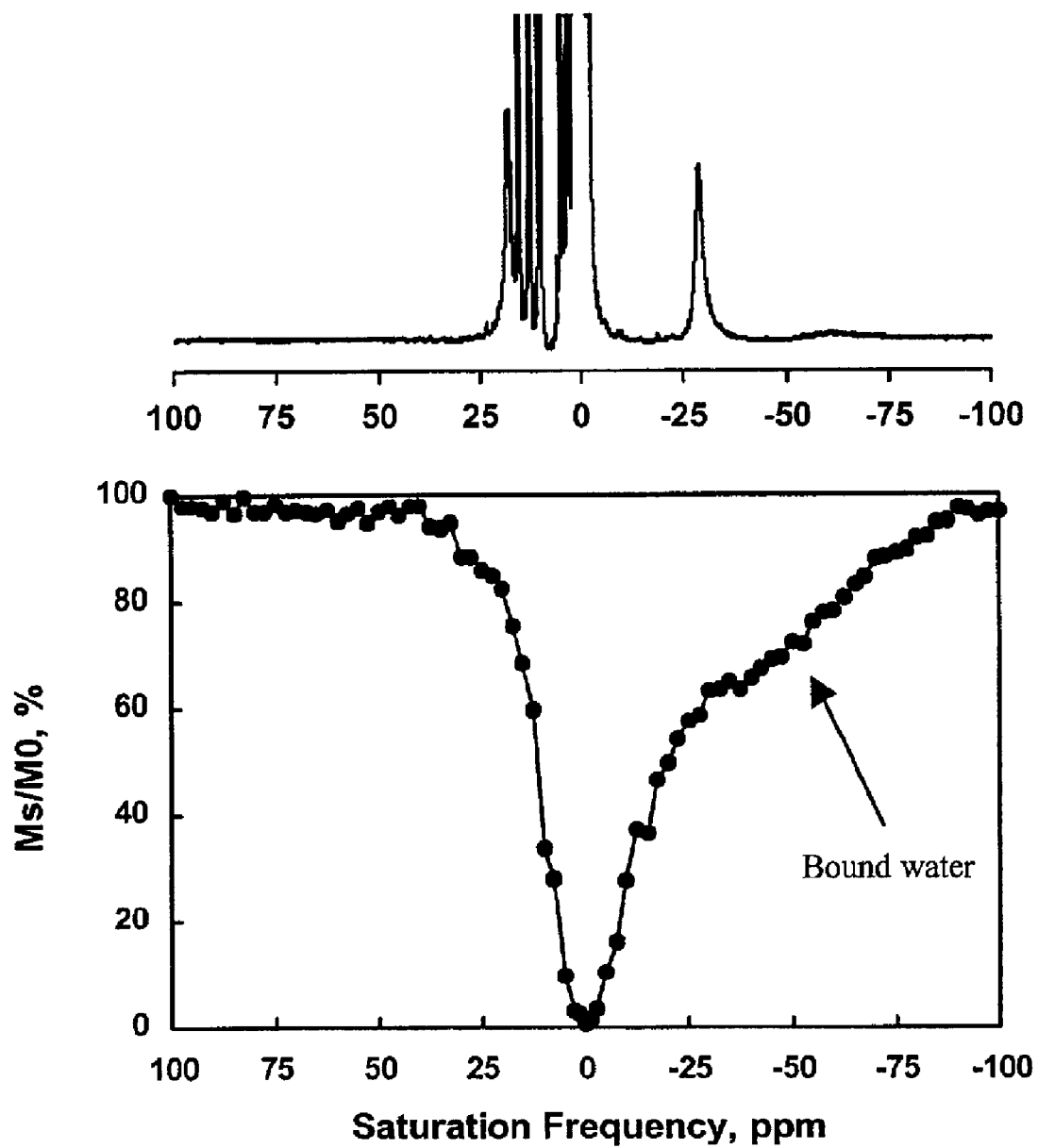
FIG. 5 illustrates an exemplary $^1$H NMR spectrum of the Pr(1)$^{3+}$ complex produced according to the present invention in the absence of a saturating pulse, and a MT profile for the complex.
Figure 6:
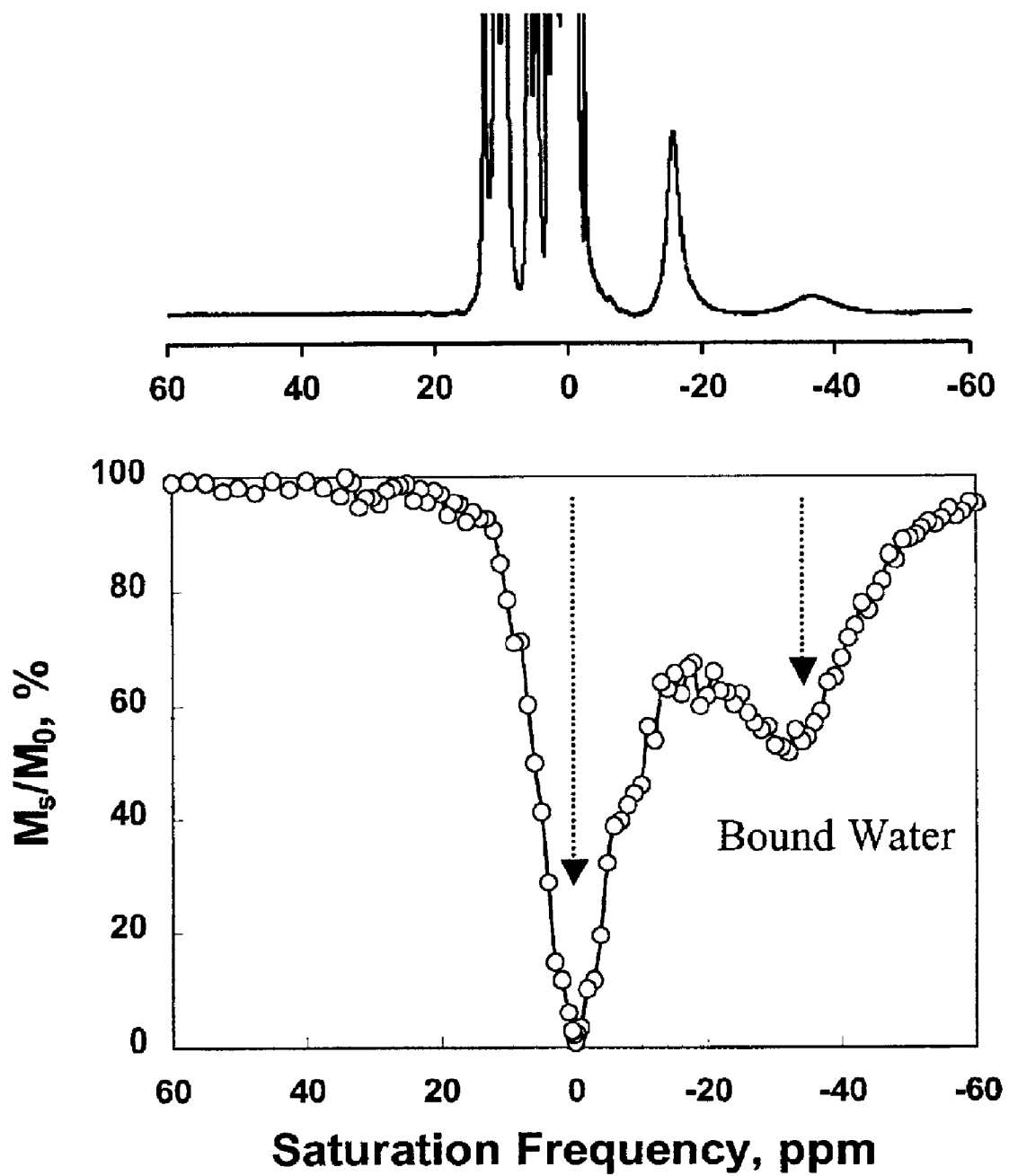
FIG. 6 illustrates an exemplary $^1$H NMR spectrum of the Nd(1)$^{3+}$ complex produced according to the present invention in the absence of a saturating pulse, and a MT profile for the complex.
Figure 7:
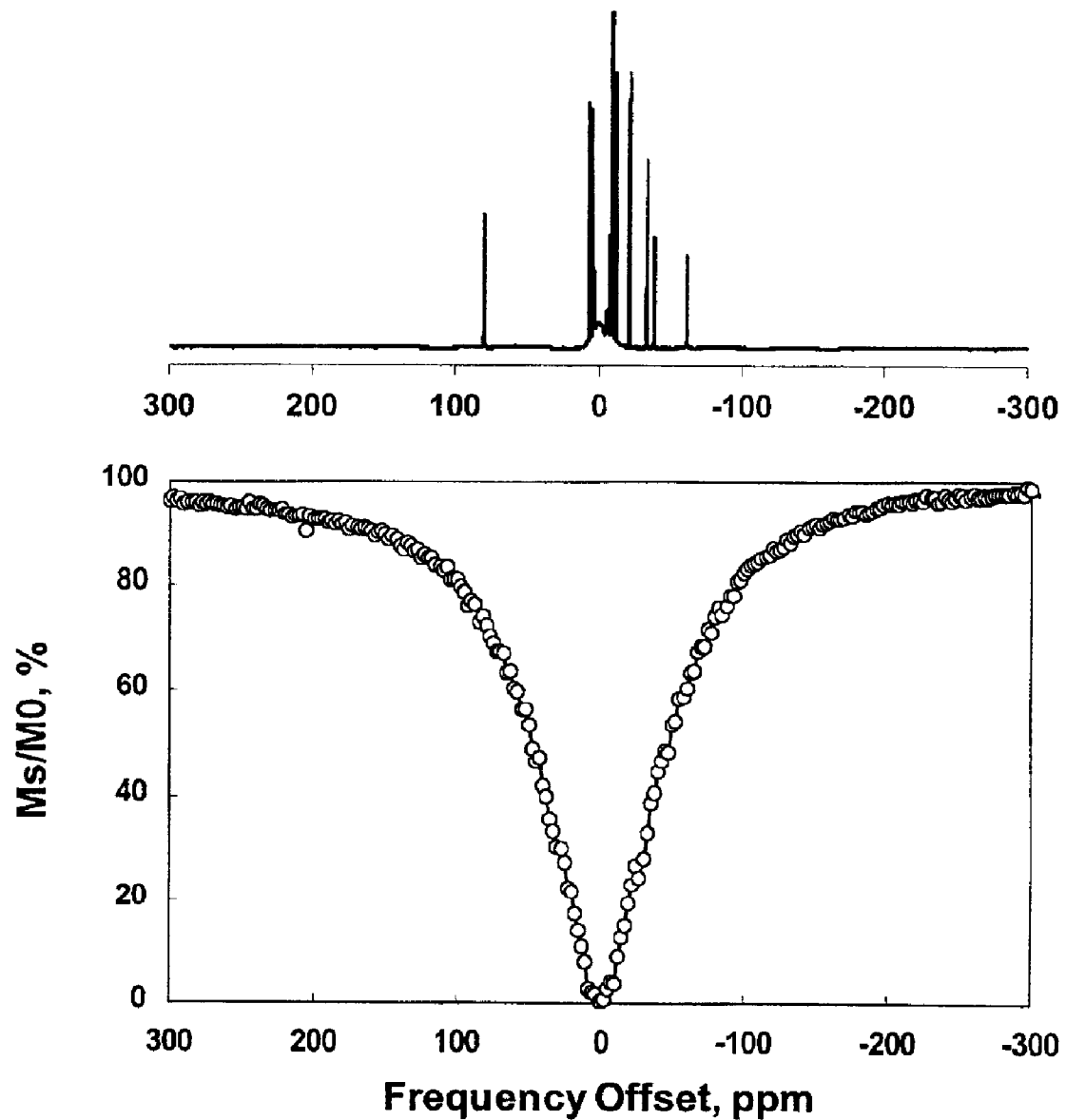
FIG. 7 illustrates an exemplary $^1$H NMR spectrum of the Yb(1)$^{3+}$ complex produced according to the present invention in the absence of a saturating pulse, and a MT profile for the complex.

In a second experiment, MT profiles, also known as Z-profiles or CEST profiles, were obtained for lanthanide-macrocylic complexes of the general formula Ln(1)$^{3+}$. FIGS. 4–7 show representative spectra in the absence of saturation (bulk water peak at 0 ppm truncated to make the bound water peaks more visible) and MT profiles for Eu(1)$^{3+}$, Pr(1)$^{3+}$, Nd(1)$^{3+}$ and Yb(1)$^{3+}$ complexes, respectively, all measured at 4.7 T. All experiments were conducted using aqueous 62.5 mM Ln(1)$^{3+}$ adjusted to neutral pH and about 22° C., using an saturation duration time of 1 s, RF power of 16 db, and a 2.5 cm surface coil. FIGS. 4, 5 and 6 illustrate that Eu(1)$^{3+}$, Pr(1)$^{3+}$ and Nd(1)$^{3+}$ all display strong MT properties when a saturating RF pulse is directed at their bound water positions of +50, −45 and −36 ppm, respectively (with bulk water at 0 ppm). Among these three complexes, Eu(1)$^{3+}$, shown in FIG. 4, had the greatest effect when the saturating pulse was centered at about 50 ppm (arrow): about a 60% decrease in the magnetization of bulk water, $M_s$, as compared to the magnetization of bulk water in the absence of a saturating pulse, $M_o$. Importantly, as indicated by a $M_s/M_o$ of about 100%, when the counter-position (i.e., −50 ppm) was saturated, there was no distortion in the bulk water signal. Of course when the saturation pulse is directed to 0 ppm (arrow) there is no signal and therefore $M_s/M_o$ is about 0%. Turning to Yb(1)$^{3+}$, theory suggests that the bound water of Yb(1)$^{3+}$ complex should be at about 200 ppm. Unfortunately, as illustrated in FIG. 7, no MT effect could be observed for this compound, probably due to its fast exchange, namely an exchange limit regime of less than one ($\Delta\omega\cdot\tau_M$=0.5).

Experiment 3

Figure 8:
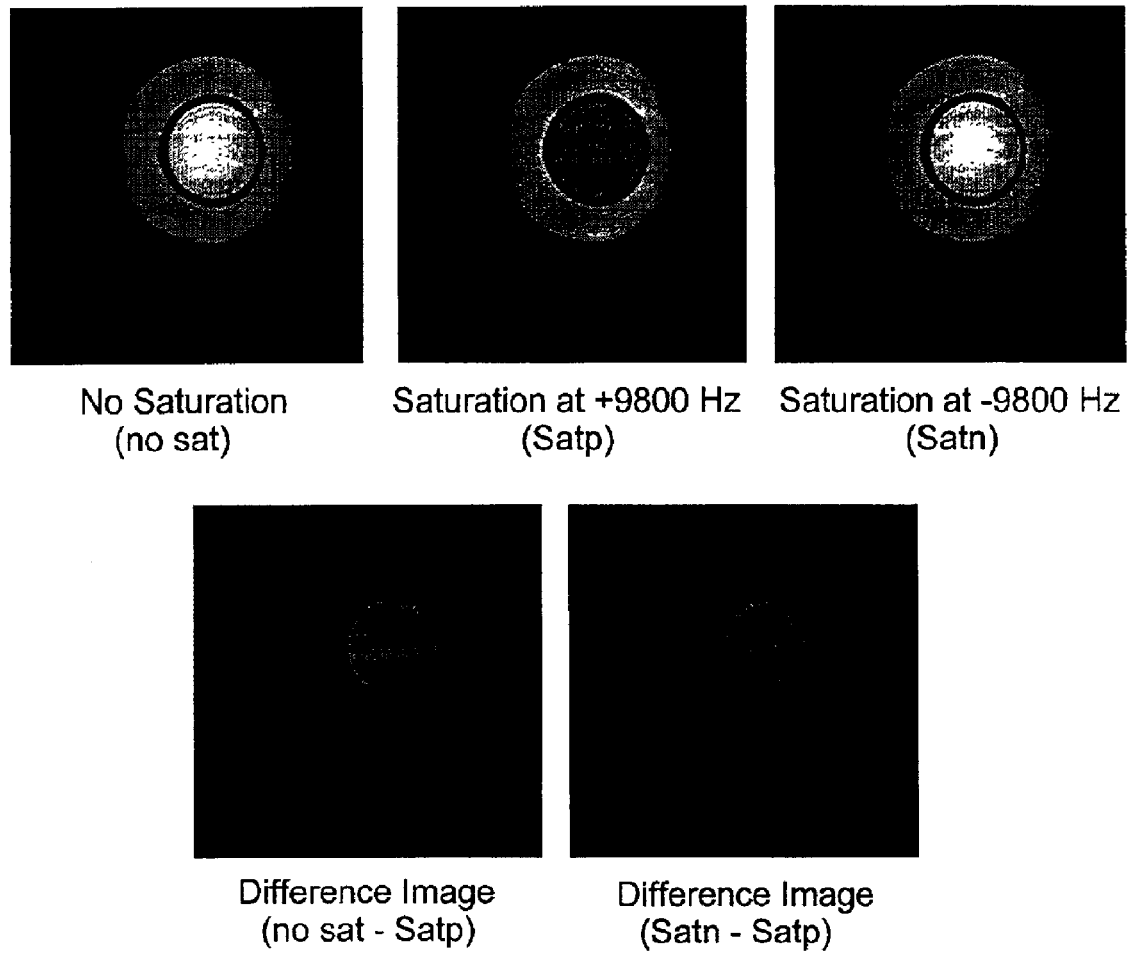
FIG. 8 illustrates exemplary MR images of a sample contained the Eu(1)$^{3+}$ complex (inner cylinder) produced according to the present invention in the absence and presence of a saturating pulse at $\pm\Delta\omega$ for bound water, and corresponding difference images.
Figure 9:
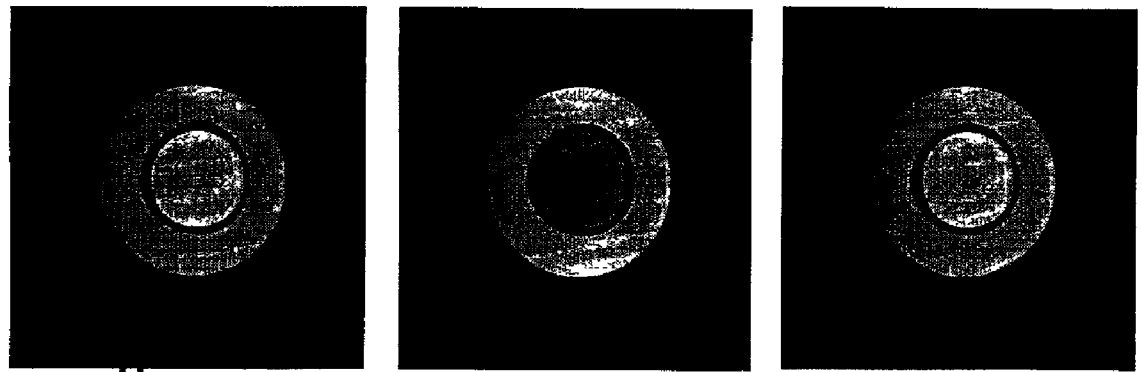
FIG. 9 illustrates exemplary MR images of a sample contained the Nd(1)$^{3+}$ complex (inner cylinder) produced according to the present invention in the absence and presence of a saturating pulse at $\pm\Delta\omega$ for bound water, and corresponding difference images.
Figure 9:
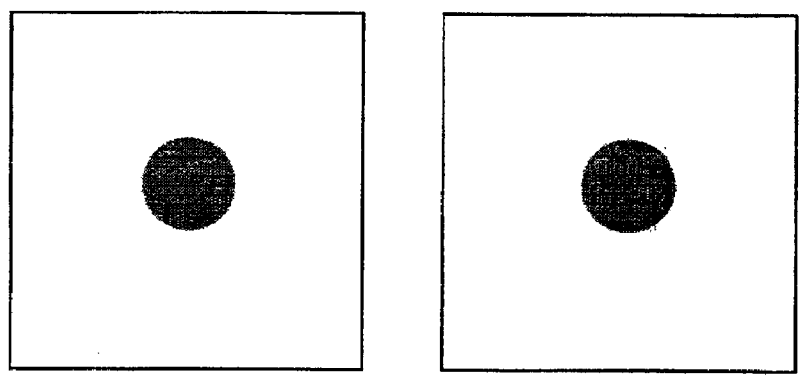

A third series of experiments was performed to examine the ability of lanthanide-macrocylic complexes of the general formula Ln(1)$^{3+}$ to enhance MRI contrast by MT. FIGS. 8 and 9 demonstrate image contrast obtained using aqueous solutions of 62.5 mM Eu(1)$^{3+}$ and Nd(1)$^{3+}$, respectively. The inner vial contains 62.5 mM Eu(1)$^{3+}$ or Nd(1)$^{3+}$ at neutral pH, while the outer vial is pure water. $T_1$-weighted spin-echo images (TR/TE=500/18 ms, 256×256 data matrix) were obtained at about 22° C. and a field strength of 4.7 T. MT was achieved by applying RE irradiation for 1 s, with a power of 16 db by using a 2.5 cm surface coil. FIG. 8 shows images obtained with no saturation (left, nosat), saturation at +9800 Hz (middle, Satp) at the resonance frequency of Eu$^{3+}$-bound water, saturation at −9800 Hz (right, satn), and the corresponding difference images. FIG. 9 shows analogous images for a phantom with no saturation (left, nosat), saturation at −6400 Hz (middle, Satp) the resonance frequency of Nd$^{3+}$-bound water, saturation at +6400 (right, satn), and the corresponding difference images. The inner vial contains 62.5 mM Nd(1)$^{3+}$ at neutral pH, while the outer vial is pure water. The irradiation duration time was 2 s, with a power of 41 db by using a 2.5 cm surface coil.

Saturating the bound water at +50 ppm for $Eu(1)^{3+}$ (FIG. 8) and −32 ppm for $Nd(1)^{3+}$ (FIG. 9) resulted in MT to bulk water, thereby providing about an 80% decrease in the bulk water signal in the inner vials without disturbing the imaging intensity of the outer vials. These levels of contrast are much better than expected for diamagnetic CAs where the resonance signal of the NH or OH group undergoing chemical exchange is only a few ppm away from the resonance signal of bulk water.

Experiment 4

Figure 10:
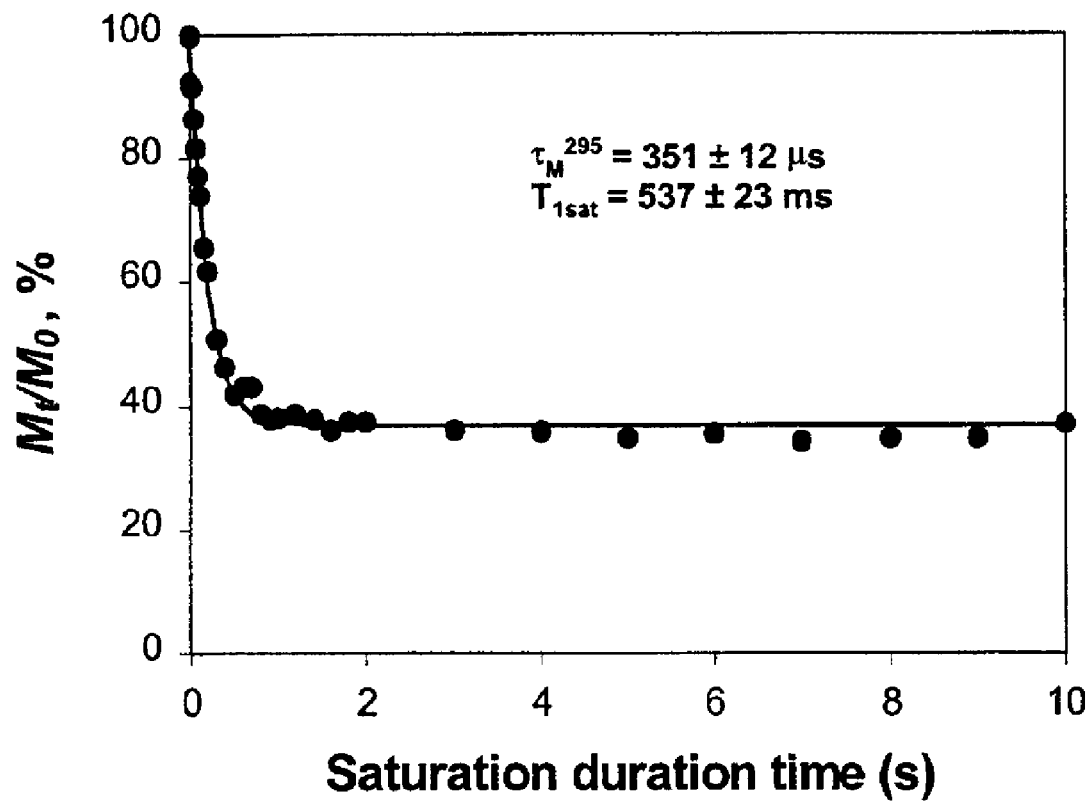
FIG. 10 illustrates an exemplary relationship of the MT effect versus saturation duration time for the Eu(1)$^{3+}$ complex.

A fourth experiment was performed under similar conditions as described for Experiments 1–3 to investigate the effect of saturation duration time and power on MT to bulk water. FIG. 10 shows the relationship of the MT effect versus saturation duration time for the $Eu(1)^{3+}$ complex. The theoretical relationship expressed in Equation (1) was fit to this data. The fits reveal that a saturation duration time of one second is sufficient to produce maximum MT effects for the $Eu(1)^{3+}$ complex. Similar analysis of data collected for $Pr(1)^{3+}$ and $Nd(1)^{3+}$ complexes revealed that a saturation duration time of about 1 to about 2 s was sufficient for these paramagnetic MT-CAs.

Figure 11:
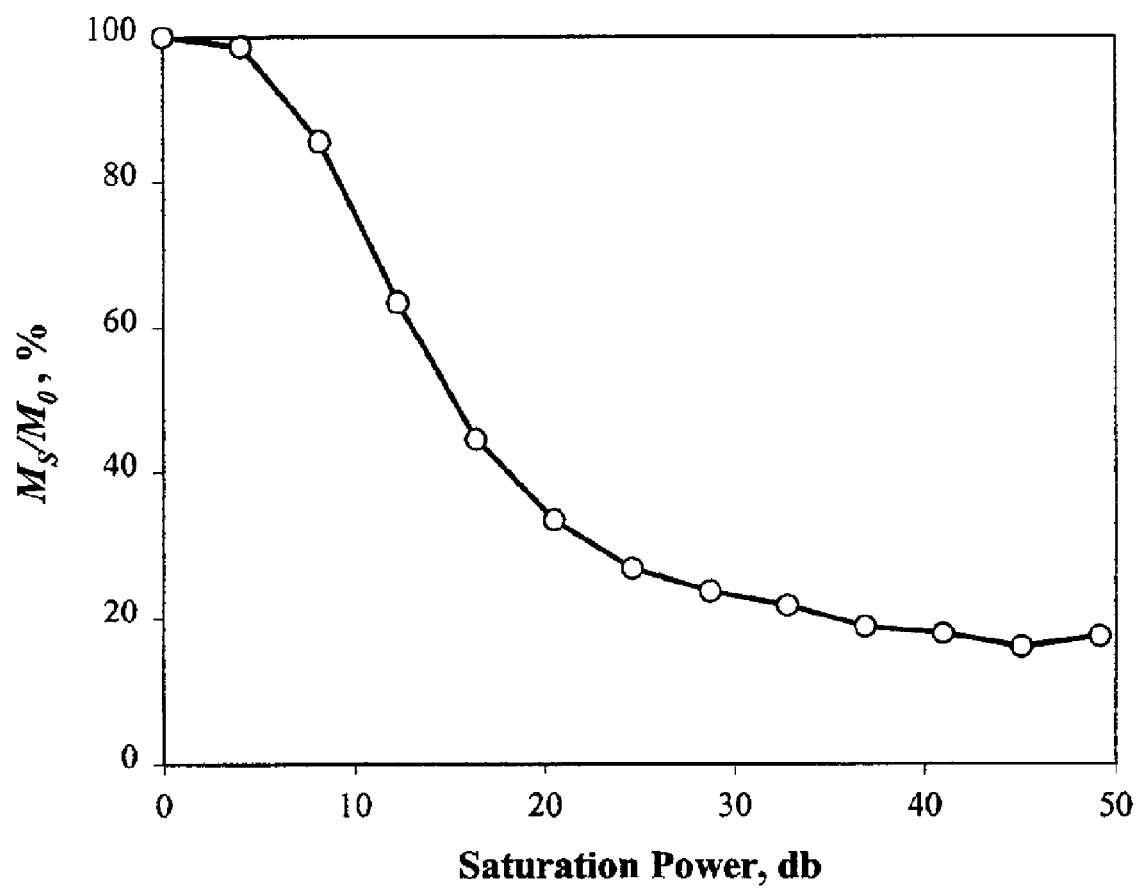
FIG. 11 illustrates an exemplary relationship of the MT effect versus saturation power for the Eu(1)$^{3+}$ complex.
Figure 12:
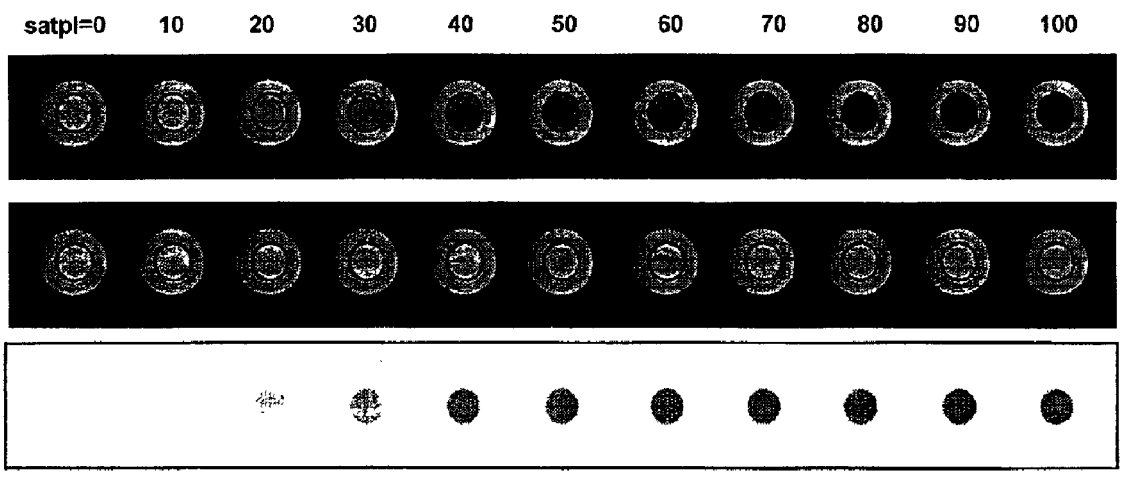
FIG. 12 illustrates exemplary MR images of a sample containing the Nd(1)$^{3+}$ complex (inner cylinder) produced according to the present invention in the absence and presence of a saturating pulse at $\pm\Delta\omega$ for bound water with different saturation powers, and corresponding difference images.

FIGS. 11 and 12 show the relationship of MT effects versus saturation power for $Eu(1)^{3+}$ and $Nd(1)^{3+}$, respectively. Saturation power level is defined as the times the maximum power of 82 db produced by 4.7 T MRI. A saturation duration time of 3 s was used for all experiments conducted on samples containing $Eu(1)^{3+}$. As illustrated in FIG. 12, saturation power levels (satpl) were increased to examine the effect of power on MT image contrast obtained using $Nd(1)^{3+}$. The irradiation duration time was 2 s, and imaging parameters included a TR/TE=500/18 ms and 64×64 data matrix. As illustrated in FIGS. 11–12, contrast continuously improved with increasing saturation power. However, a practical limit of 30–50 db was found for these CAs given the MRI scanner used in these experiments. Other considerations, such as heating of biological or other heat sensitive samples, due to RF power deposition may also limit the saturation power applied. The CA of the present invention are stable to temperatures of at least 100° C.

Experiment 5

A fifth series of experiments was conducted on a lanthanide-macrocylic complex of the present invention, and having the general formula, $Eu(2)^-$, where the four pendent arms R, R', R" and R'" are all carboxyl-acetamidoacetate, (i.e., LnDOTA-4AmC⁻) as depicted below:

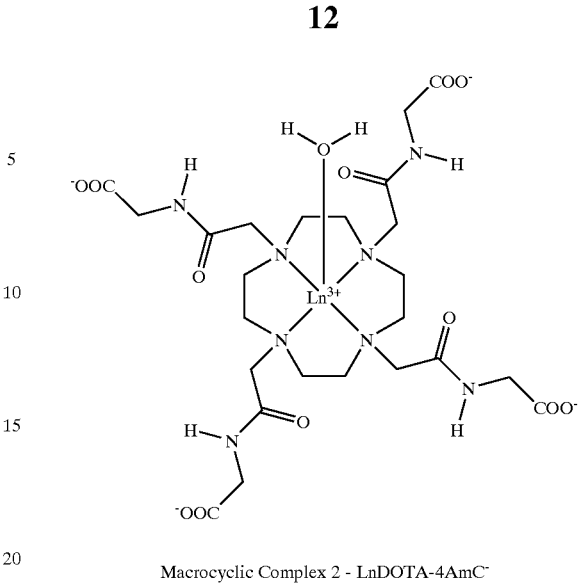

Macrocyclic Complex 2 - LnDOTA-4AmC⁻

Figure 13:
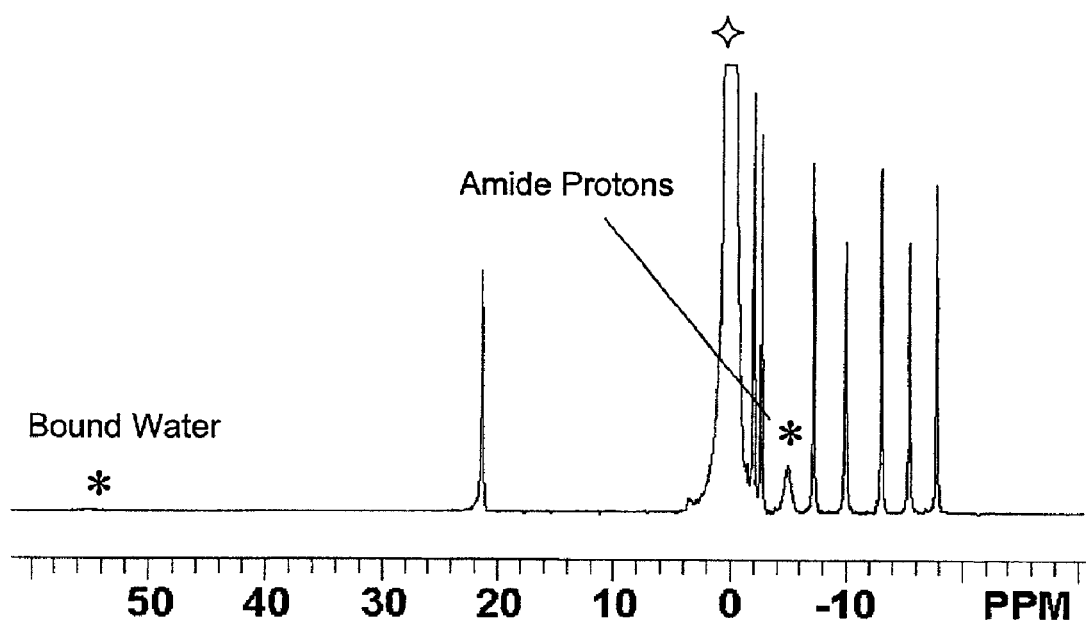
FIG. 13 illustrates an exemplary $^1$H NMR spectrum of the Eu(2)$^-$ complex produced according to the present invention in the absence of a saturating pulse.

FIG. 13 shows a 500 MHz 1H NMR spectrum of $Eu(2)^-$ complex in an aqueous solution adjusted to pH 7.4 and 25° C. Two sites in the complex (denoted by the symbols *) are chemically exchangeable with bulk water (denoted by the symbol ◊): one is from $Eu^{3+}$-bound water at about 57 ppm, and another is from four equivalent amide protons on the pendent arms at about −6 ppm.

Experiment 6

Figure 14:
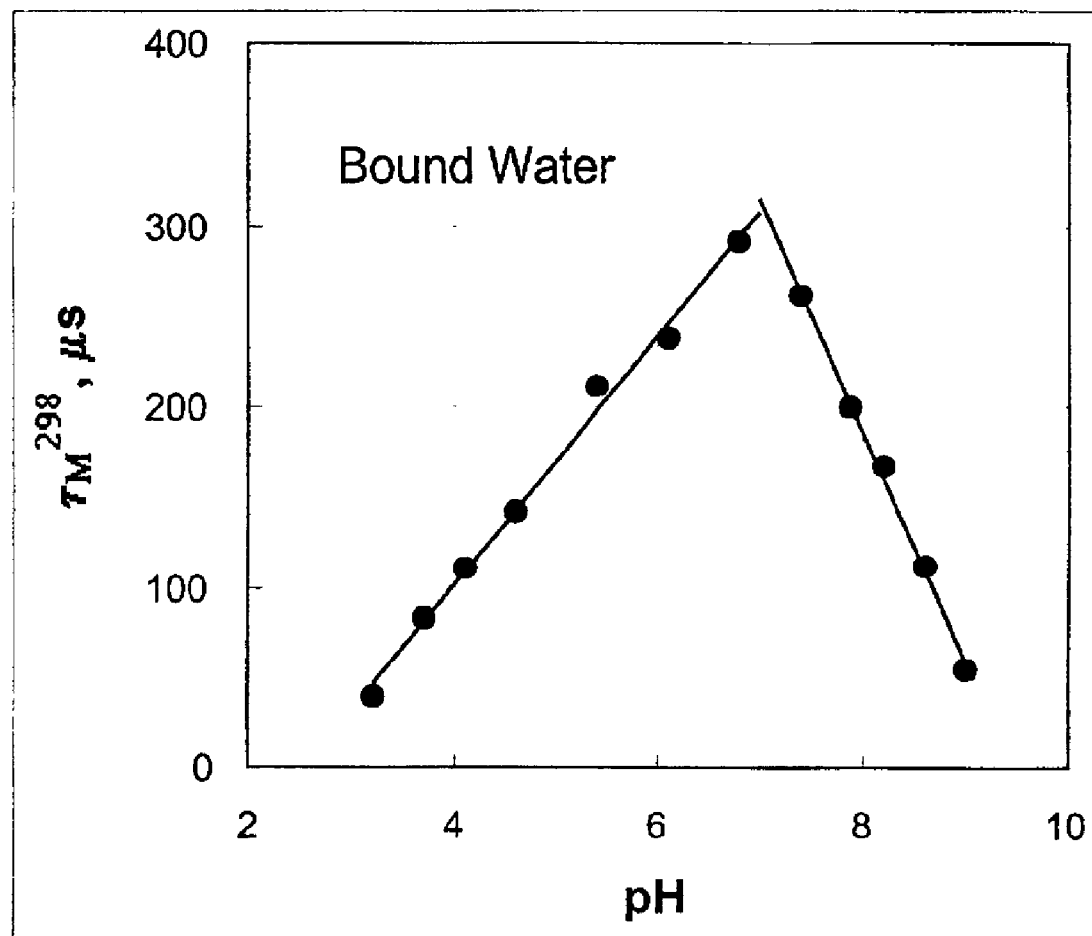
FIG. 14 illustrates an exemplary relationship the pH dependence of the $\tau_M^{298}$ for the bound water molecule of the Eu(2)$^-$ complex of the present invention.
Figure 15:
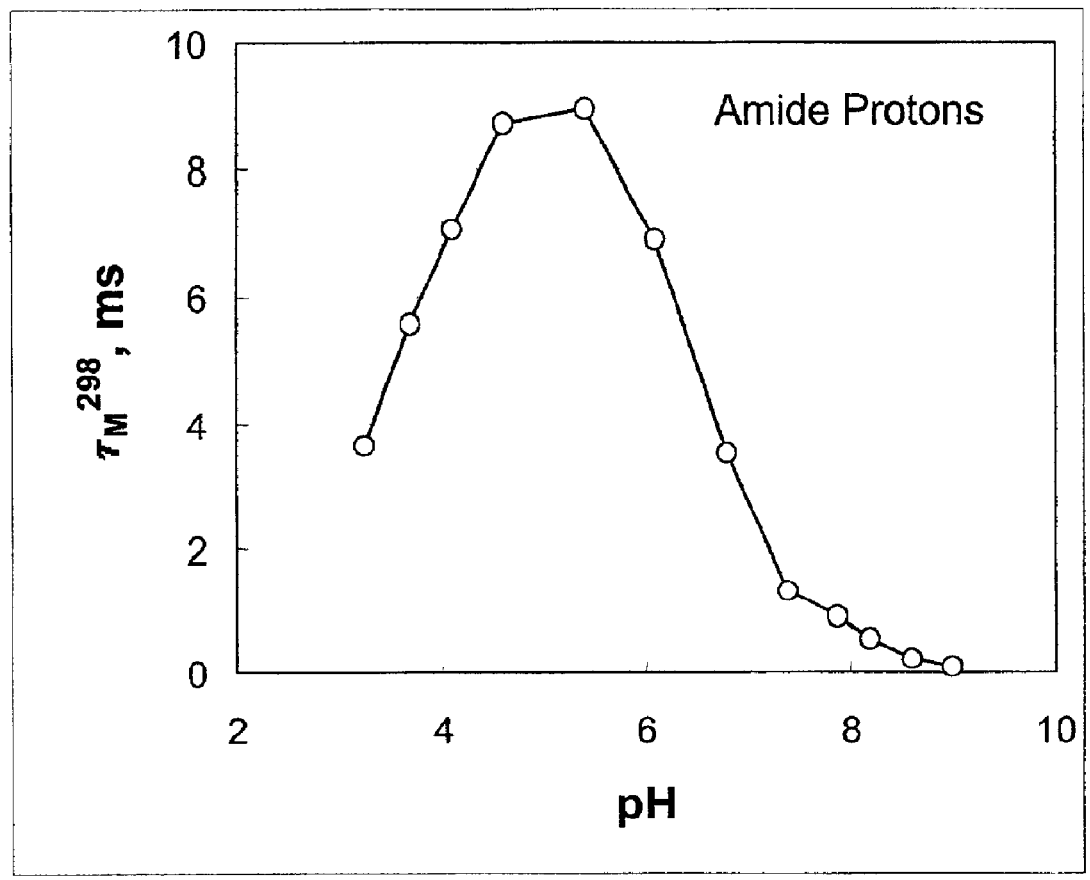
FIG. 15 illustrates an exemplary relationship the pH dependence of the $\tau_M^{298}$ for protons associated with the amides in the pendent arms of the Eu(2)$^-$ complex of the present invention.

In a sixth series of experiments, the pH dependence of the bound water (FIG. 14) and the amide (FIG. 15) protons lifetimes, $\tau_M^{298}$, were determined by variable temperature 1H NMR line width fitting. The chemically exchangeable bound water and amide protons have different dependence on pH. For bound water protons, the slowest exchange, i.e., largest $\tau_M^{298}$, takes place at pH 7 (FIG. 14). Moreover, the pH dependence may be divided into two linear ranges: an acidic range where $\tau_M^{298}$=68.6*pH−172.5; and a basic range where $\tau_M^{298}$=−128.2*pH+1212.6, respectively. For the amide protons, the slowest exchange is at pH 5.5 (FIG. 15). In addition, the exchange limiting regimes ($\Delta\omega \cdot \tau_M$) calculated from the above data, for the magnetic field strength of 4.7, are all larger than 1, thus indicating that either the bound water or amide protons chemical exchange sites may serve as MT-CAs.

Experiment 7

Figure 16:
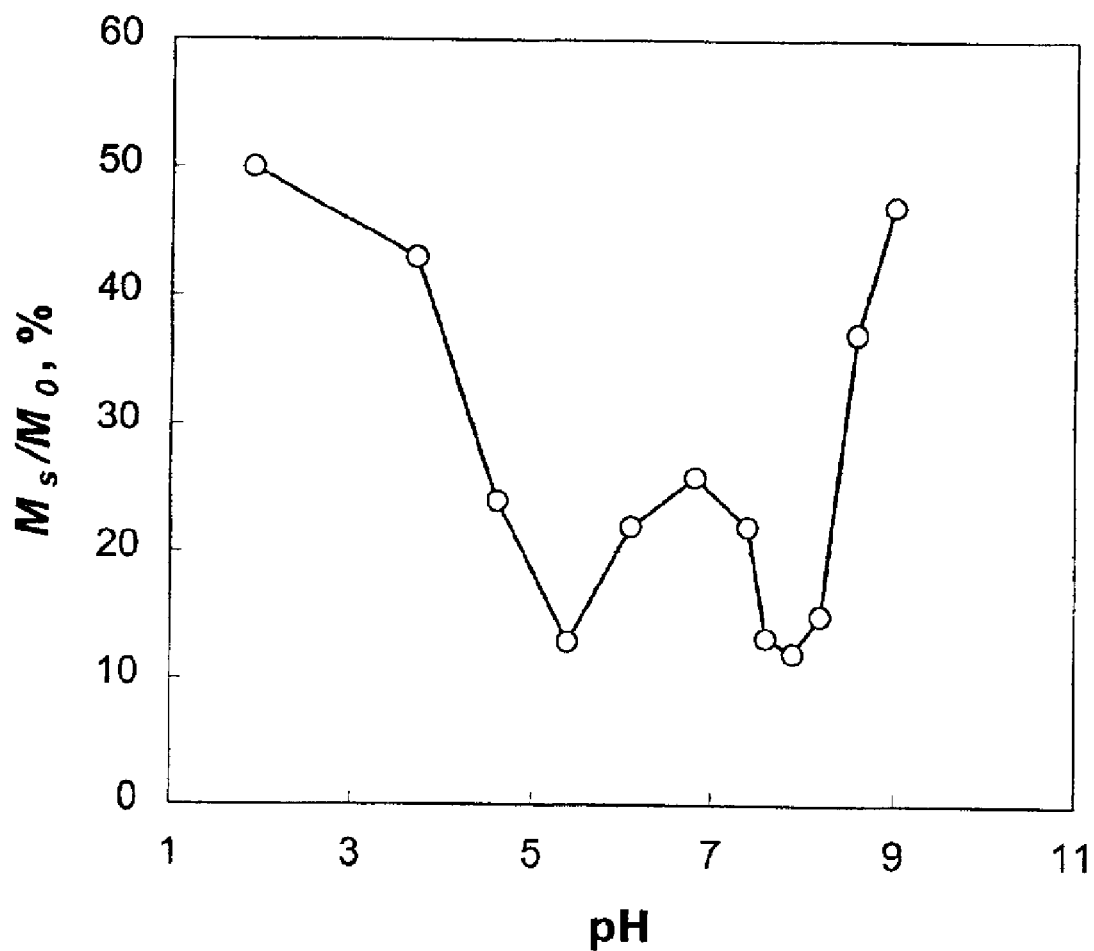
FIG. 16 illustrates the pH dependence of the MT effect obtained when saturating the bound water molecule of the Eu(2)$^-$ complex of the present invention.
Figure 17:
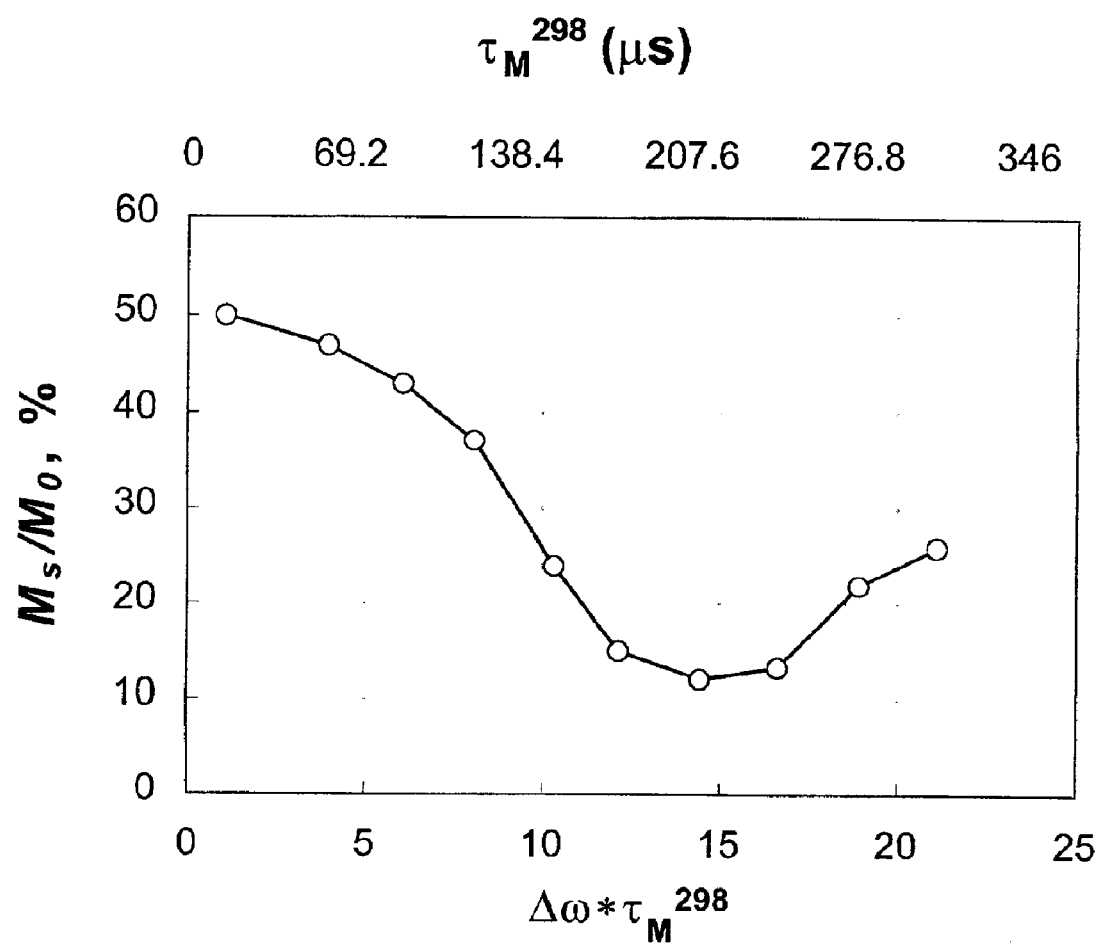
FIG. 17 illustrates the relationship between the MT effect obtained when saturating the bound water molecule of the Eu(2)$^-$ and the bound water lifetime, $\tau_M^{298}$, or the exchange limiting regime, $\Delta\omega \cdot \tau_M$.
Figure 18:
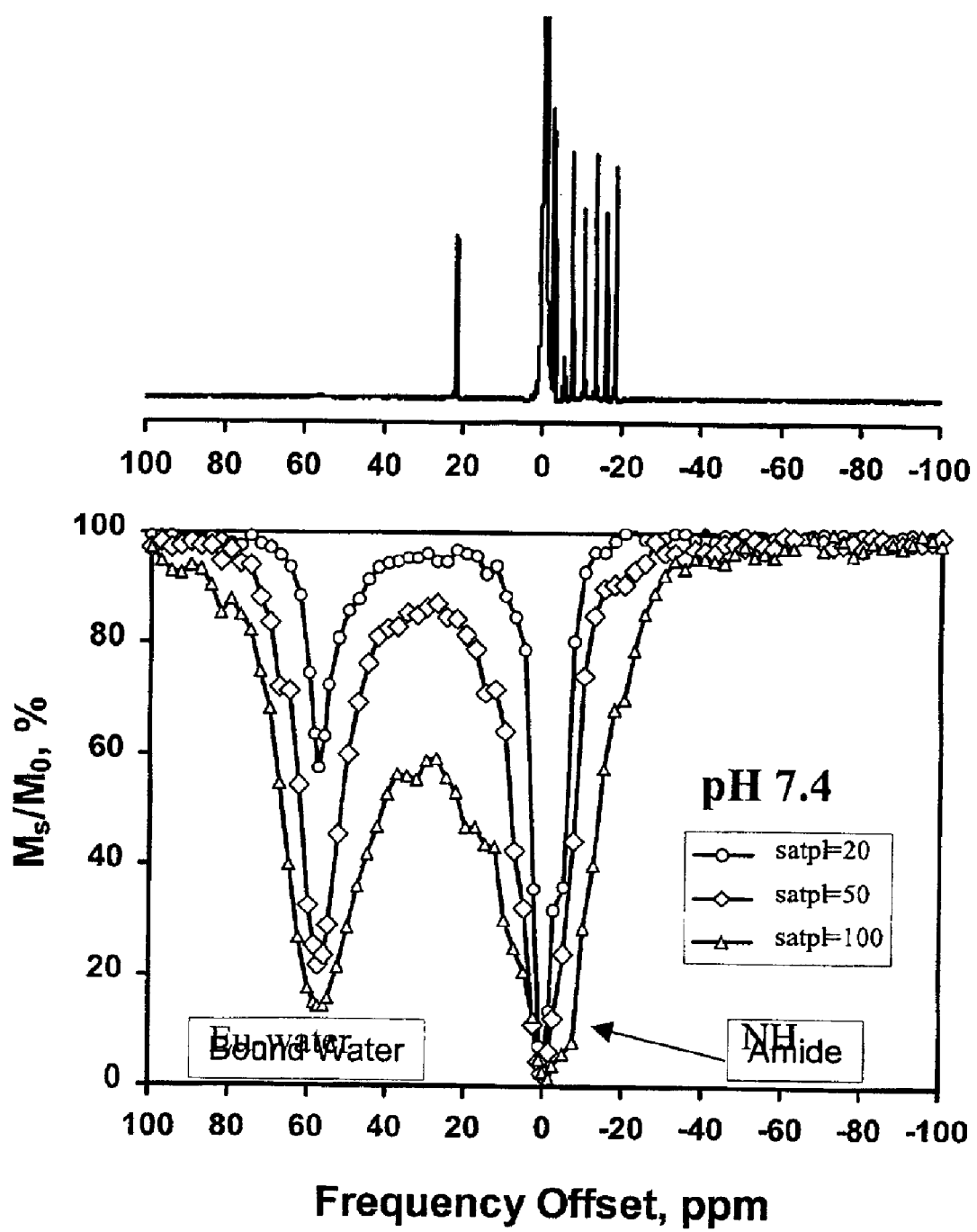
FIG. 18 illustrates an exemplary $^1$H NMR spectrum of the Eu(2)$^-$ complex produced according to the present invention in the absence of a saturating pulse, and a MT profile for the complex produced at three different levels of saturating power.

In a seventh experiment, MT profiles were obtained for 62.5 mM aqueous solutions of the $Eu(2)^-$ lanthanide-macrocylic complex. A saturating RF pulse of 2 s at the resonance frequency of bound water or amide protons, with a power of 41 db, was applied to a 3.5 cm volume coil. FIG. 16 shows that MT decreases were produced for $Eu(2)^-$ by saturating bound water proton at about 57 ppm throughout the pH range of 3 to 9. As illustrated in FIG. 16, the magnitude of MT decrease has a complex dependence upon pH. The same set of data was plotted versus the bound water lifetime, $\tau_M^{298}$, or the exchange limiting regime, $\Delta\omega \cdot \tau_M$, as shown in FIG. 17. The largest MT occurs for a $\Delta\omega \cdot \tau_M$ ranging from about 12 to about 17, and optimally about 15. FIG. 18 further demonstrates that the MT effect continues to increase with the magnitude of saturation power applied, up to the maximum power (satpl=100; corresponding to 82 db) allowed by the MRI instrumentation used in the experiment.

Experiment 8

Figure 19:
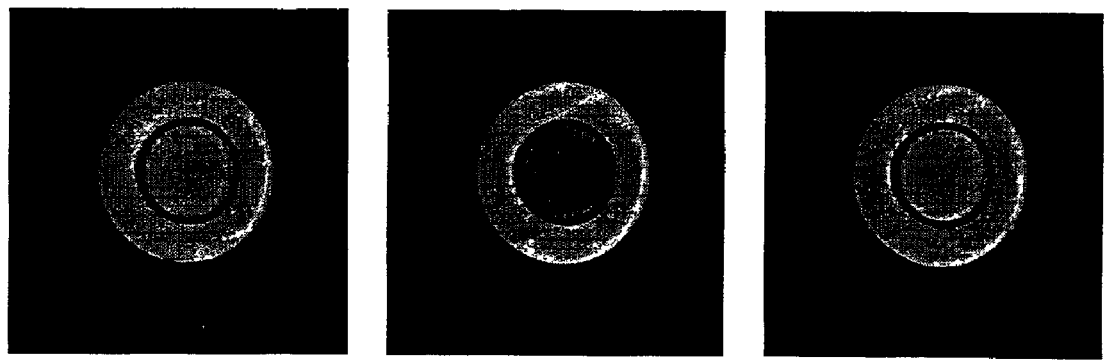
FIG. 19 illustrates exemplary MR images of a sample containing the Eu(2)$^-$ complex (inner cylinder) produced according to the present invention in the absence and presence of a saturating pulse at $\pm\Delta\omega$ for bound water, and corresponding difference images.
Figure 19:
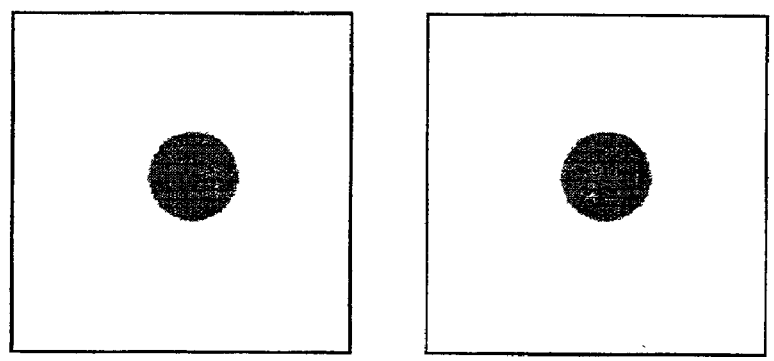
Figure 20:
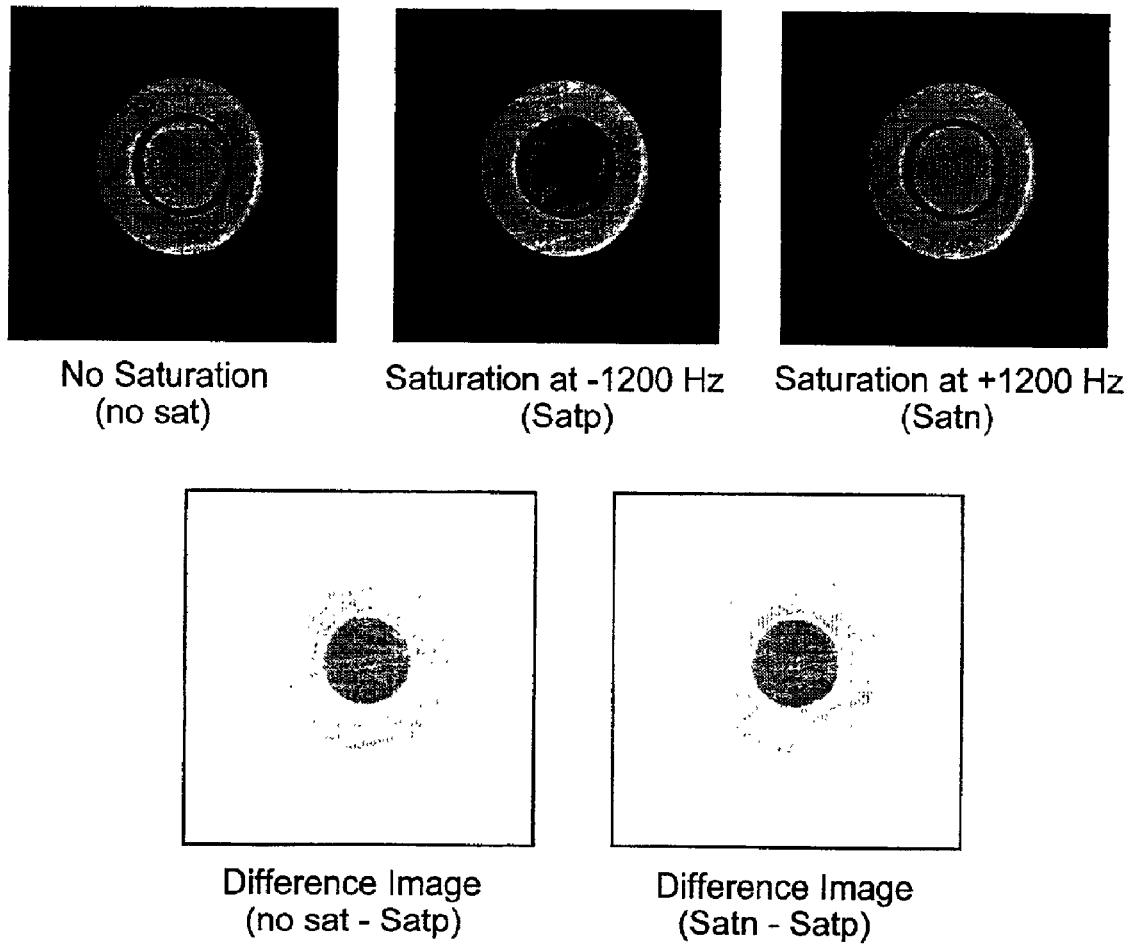
FIG. 20 illustrates exemplary MR images of a sample containing the Eu(2)$^-$ complex (inner cylinder) produced according to the present invention in the absence and presence of a saturating pulse at $\pm\Delta\omega$ for amide protons, and corresponding difference images.

An eighth series of experiments was performed to examine the ability of the Eu(2)⁻ lanthanide-macrocylic complex to enhance MRI contrast by MT. Images and difference images were collected under conditions similar to that described for Experiment 3, using a sample comprising a inner vial of 62.5 mM Eu(2)⁻ and outer vial of water. FIGS. 19 and 20 are MT images obtained while saturating either the bound water or amide protons, respectively. These figures show that the MR signal of either chemically exchangeable protons may be saturated individually to provide large MT contrasts. For saturation of amide protons, however, a lower saturation power was preferred to avoid direct saturation of the bulk water MR signal. Importantly, by virtue of its farther distance from the bulk water MR signal, higher levels of saturating power, and therefore greater MT contrast, may be obtained by saturating the bound water proton MR signal than that obtained by saturating the amide protons. This point is further illustrated in Experiment 9.

Experiment 9

Figure 21:
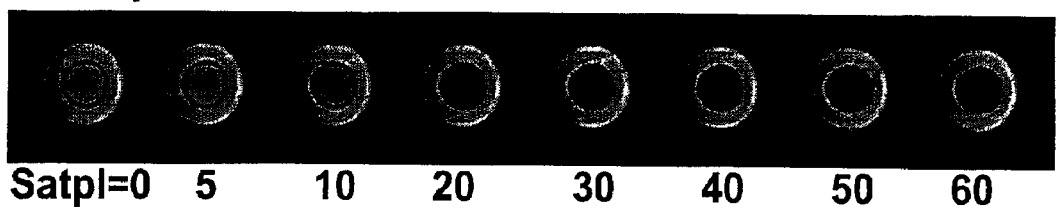
FIG. 21 illustrates exemplary MR images of a sample containing the Eu(2)$^-$ complex (inner cylinder) produced according to the present invention in the absence and presence of a saturating pulse at $\pm\Delta\omega$ for bound water with different saturation powers, and corresponding difference images.
Figure 21:
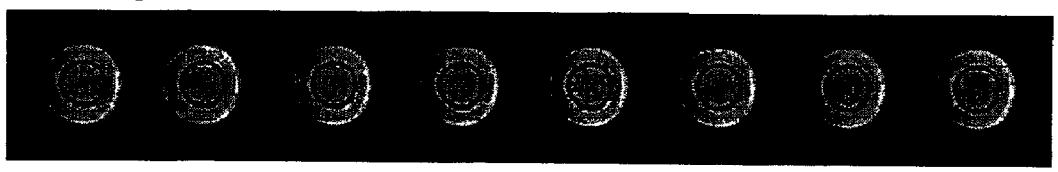
Figure 21:
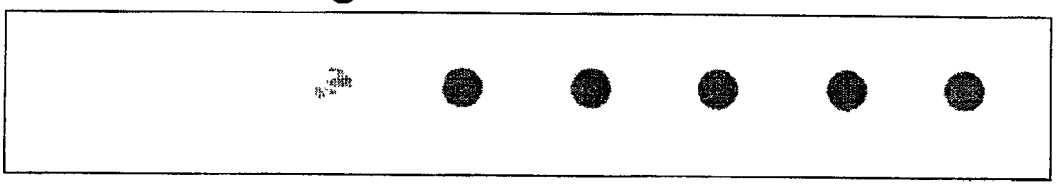
Figure 22:
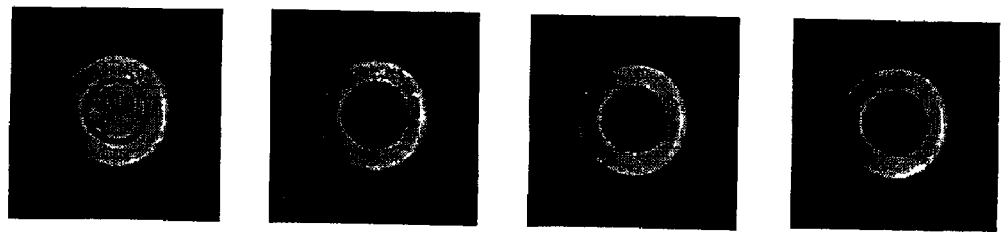
FIG. 22 illustrates exemplary MR images of a sample containing the Eu(2)$^-$ complex (inner cylinder) produced according to the present invention in the presence of a saturating pulse at $\pm\Delta\omega$ for amides protons, and corresponding difference images.
Figure 22:
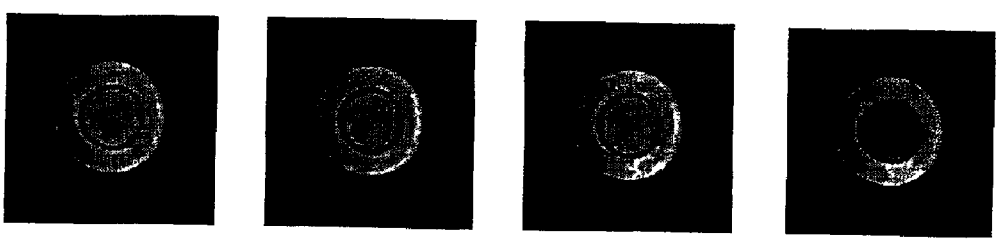
Figure 22:
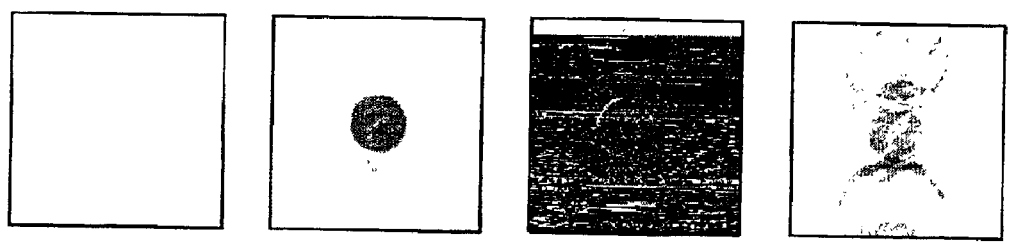

In a ninth series of experiments, analogous to Experiment 4, the effect of saturation power on MT to bulk water using the Eu(2)⁻ lanthanide-macrocylic complex was examined. As illustrated in FIG. 21, a saturating RF pulse was applied at: a) the resonance frequency of bound-water (i.e., satfreq=+11500 Hz), and b) an equal frequency away from the bulk water signal but opposite to the bound water signal (i.e., satfreq=−11500 Hz). The difference image (series c) is shown below. As saturation power level (satpl) was increased, image contrast continuously improved. In comparison, when the amide protons of Eu(2)⁻ were saturated, as illustrated in FIG. 22, as power levels were increased there are serious imaging distortions, mostly likely due to direct saturation of the bulk water.

Experiment 10

A tenth experiment was conducted on a lanthanide-macrocylic complex of the present invention, and having the general formula, Ln(9)$^{3+}$, where the four pendent arms R, R', R" and R'" are all acetamidoacetate (i.e., LnDOTA-4Am$^{3+}$), as depicted below:

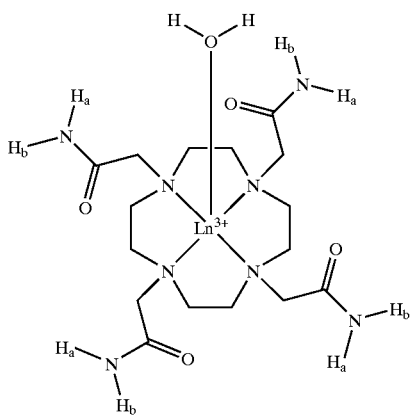

Macrocyclic Complex 9 - LnDOTA-4Am$^{3+}$

Figure 23:
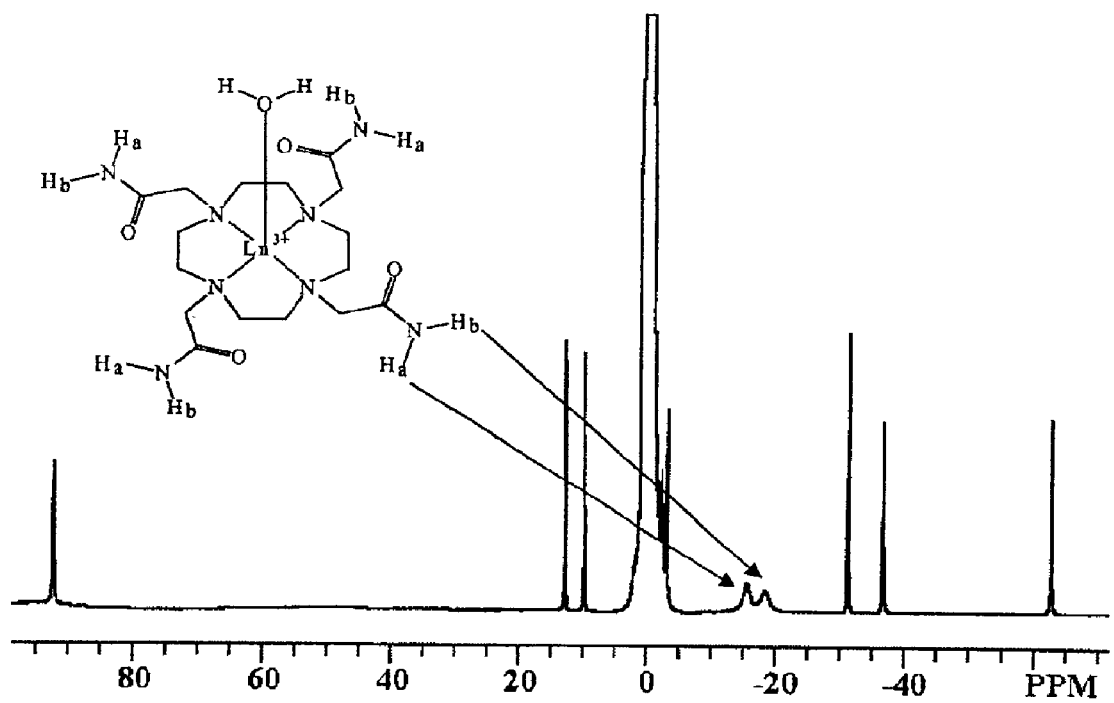
FIG. 23 illustrates an exemplary $^1$H NMR spectrum of the Yb(9)$^{3+}$ complex produced according to the present invention in the absence of a saturating pulse.

For certain Ln(9)$^{3+}$ complexes, for example, with Ln equal to Yb or Tm, the bound water molecules are $^1$H NMR invisible probably due to the fast exchange between the bound water and the bulk water. However, these complexes are still preferred MT CAs because their $^1$H NMR spectra present two sets of amide protons (for example, −14.5 and −17.7 ppm for Yb(9)$^{3+}$, and −42 and −52 ppm for Tm(9)$^{3+}$, respectively), which could be saturated to produce MT contrast. FIG. 23 shows a high resolution $^1$H NMR spectrum of an aqueous solution containing Yb(9)$^{3+}$ adjusted to pH 7.4 and 25° C. Theoretical prediction indicates that a bound water should resonate at about 200 ppm. Unfortunately, the NMR signal was invisible, probably due to its fast exchange with the bulk water. However, the eight exchangeable amide protons present as two resonance peaks with equivalent intensity, at −14.5 ($H_a$) and −17.7 ($H_b$) ppm, respectively, are visible.

Figure 24:
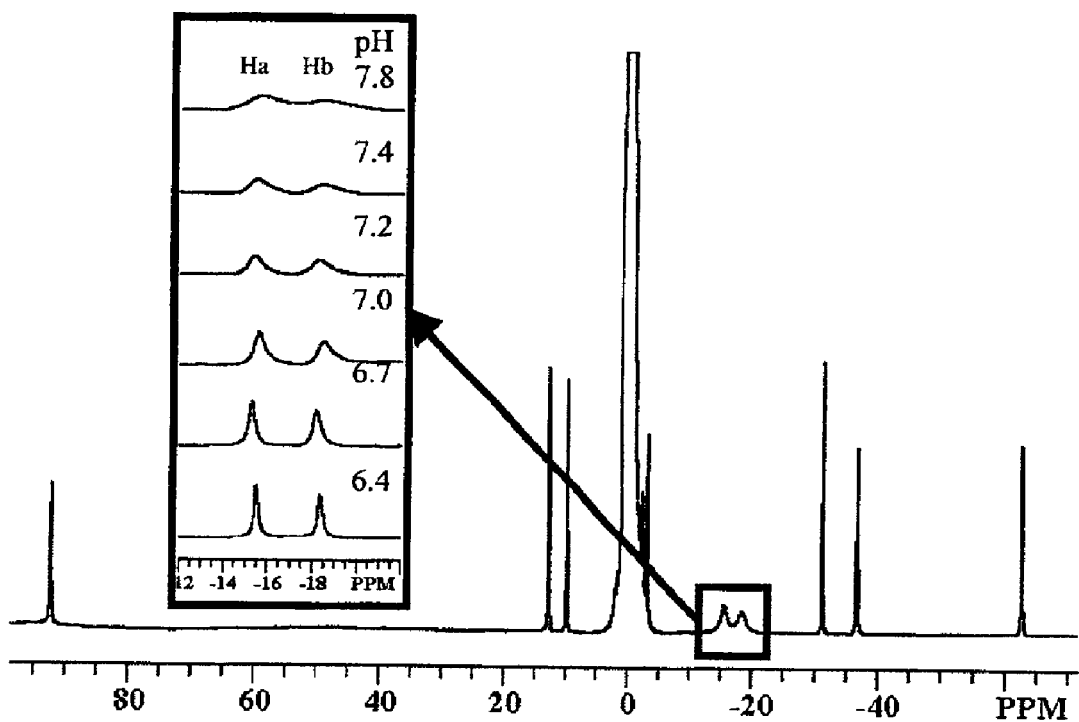
FIG. 24 illustrates an exemplary $^1$H NMR spectra of the Yb(9)$^{3+}$ complex produced according to the present invention in the absence of a saturating pulse and at different sample pH.
Figure 25:
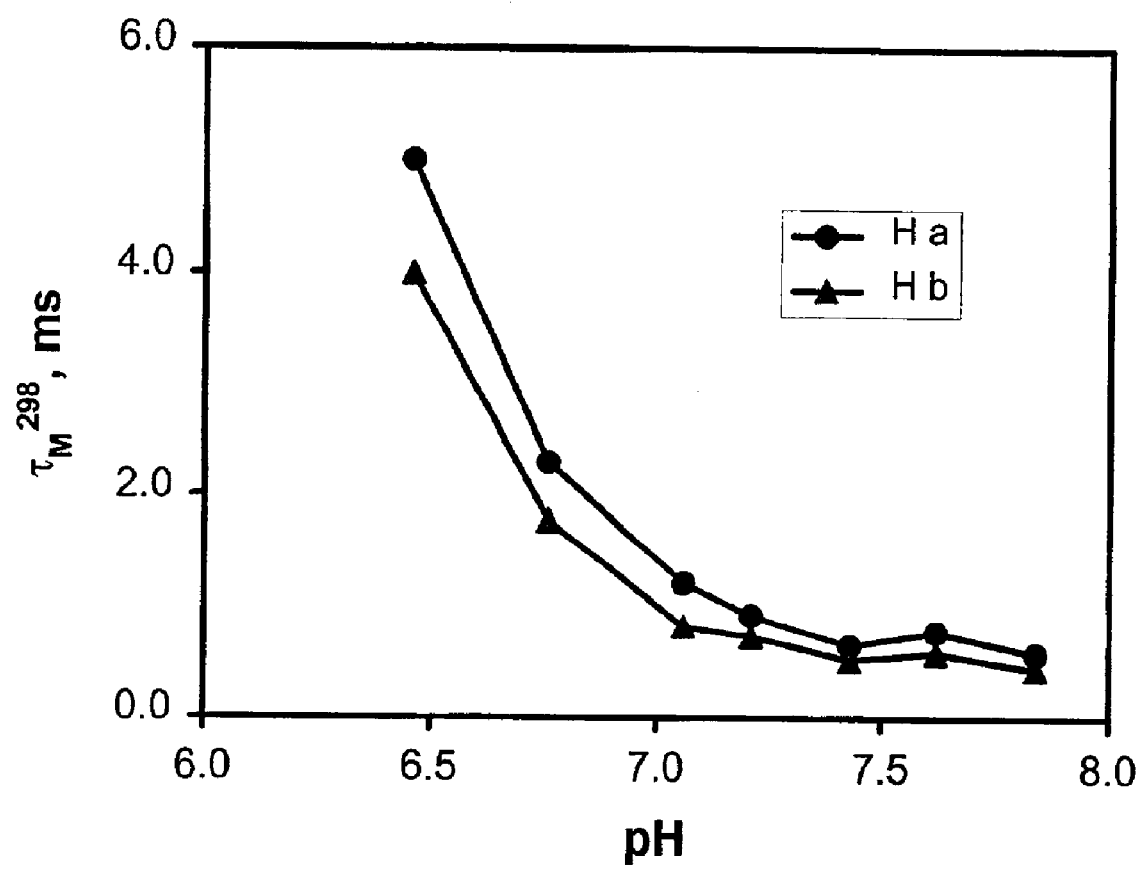
FIG. 25 illustrates an exemplary relationship of the pH dependence of the $\tau_M^{298}$ for protons $H_a$ and $H_b$ associated with the amides in the pendent arms of the Yb(9)$^{3+}$ complex of the present invention.

As indicated by their linewidths, illustrated in FIG. 24, the two exchangeable amide sites have different dependences upon pH. As further illustrated in FIG. 25, $H_b$ exchanges about 1.3 times faster than that of $H_a$. The exchange limiting regimes, $\Delta\omega\cdot\tau_M$, of both amide protons at magnetic field strength of 7.05 T are much larger that 1, for a broad range of pH values indicating that Ln(9)$^{3+}$ complexes in general may be suitable as MT-CAs (TABLE 2). Similar to that discussed above for Ln(1)$^{3+}$, either too fast or too slow exchange may produce less MT. For the conditions used to obtain the data presented in Table 2, the maximum MT effect appear to be obtained for Ln(9)$^{3+}$ complexes when the exchange limiting regime is about 15.

TABLE 2

| pH | $\tau_M^{298}$, ms | | $\Delta\omega\cdot\tau_M^{298}$ | |
|---|---|---|---|---|
|  | $H_a$ | $H_b$ | $H_a$ | $H_b$ |
| 6.46 | 5.00 | 4.00 | 139.3 | 133.7 |
| 6.76 | 2.30 | 1.78 | 64.1 | 59.5 |
| 7.06 | 1.21 | 0.82 | 33.6 | 27.2 |
| 7.21 | 0.92 | 0.72 | 25.5 | 24.2 |
| 7.43 | 0.64 | 0.52 | 17.9 | 17.4 |
| 7.84 | 0.57 | 0.44 | 15.9 | 14.7 |

Experiment 11

Figure 26:
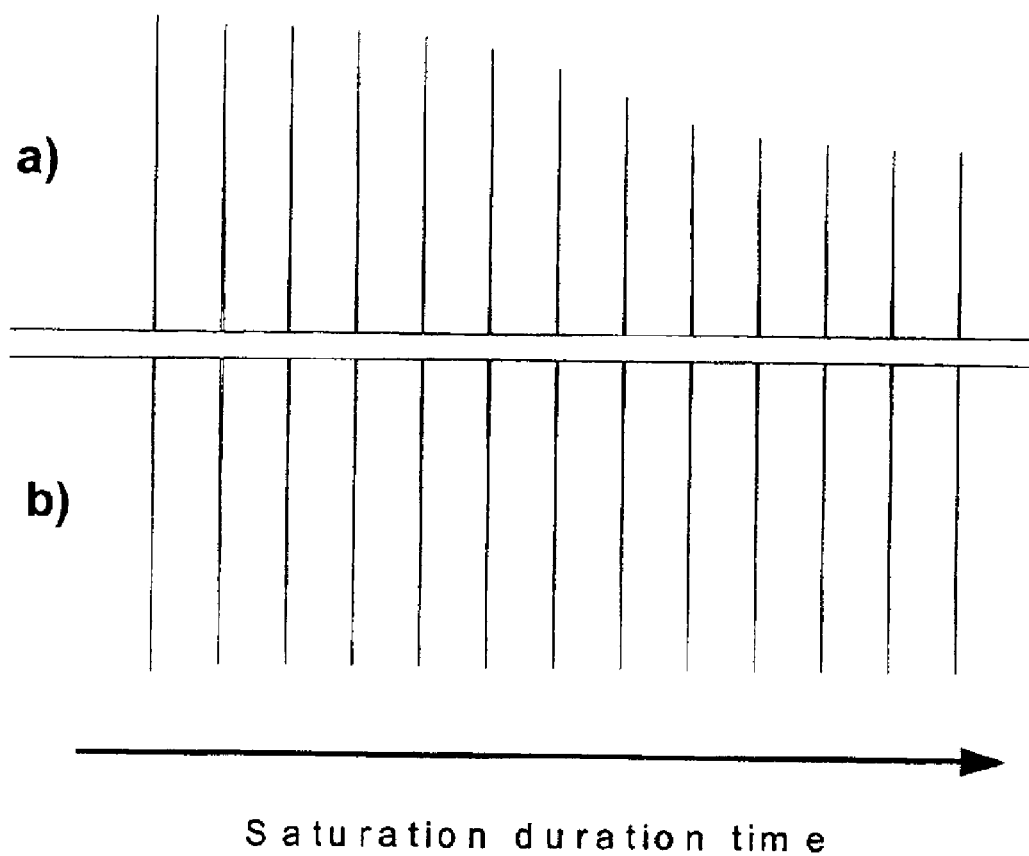
FIG. 26 illustrates an exemplary a series of bulk water $^1$H NMR spectra obtained for an aqueous solution of Yb(9)$^{3+}$ complex of the present invention obtained while applying a saturating pulse of different duration and centered between the resonance signal of the $H_a$ and $H_b$ associated with the amides in the pendent arms of the complex.

An eleventh series of experiments was conducted to examine the effect of saturation duration on the magnitude of MT obtained using the Yb(9)$^{3+}$ complex. FIG. 26 shows a series of bulk water $^1$H NMR spectra obtained for an aqueous solution of 5 mM Yb(9)$^{3+}$ adjusted to pH 7.4 and 25° C. The upper series of spectra (a) were obtained while applying a saturating pulse of different duration and centered between the resonance signals of the exchangeable amide protons, with a saturating bandwidth of 1500 Hz. The saturating bandwidth was produced using conventional water elimination technique (i.e., a wet1d pulse sequence). See Varian User Manual; Varian NMR, Palo Alto, Calif.; User Guide, VNMR Version 6.1 software, 1997), incorporated herein by reference. The pulse sequence to produce saturation was modified to include hard loops to shape the pulse train (90° e-burp1, typically repeated from about 0 to about 500 times) with a bandwidth of 1500 Hz (pwwet=3.0 ms and wetpwr=28 db). The lower series (b) of spectra, shown inverted to facilitate comparison to series (a), were obtained while applying the same saturating pulse, but on the opposite side and equal distance away from the bulk water MR signal. As the illustrated in FIG. 26, for a saturating pulse of about 2 s or longer, about a 38% decrease in the bulk water signal was obtained for series (a). In comparison, there was substantially no decrease in the bulk water signal for series (b).

Experiment 12

Figure 27:
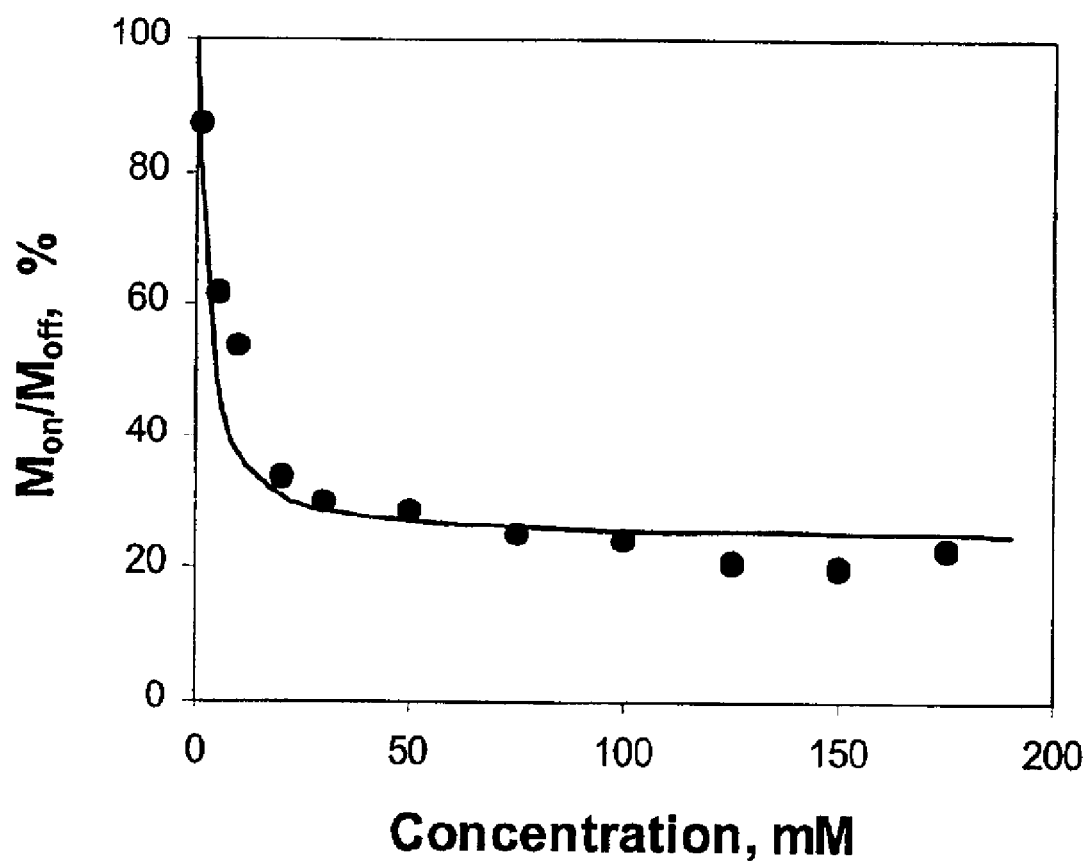
FIG. 27 illustrates an exemplary relationship between the MT effect obtained for different concentrations of the Yb(9)$^{3+}$ complex of the present invention.

A twelfth series of experiments was conducted to examine the effect of the $Yb(9)^{3+}$ concentration on the magnitude of MT-based contrast. The concentration dependence of the MT effect obtained for the $Yb(9)^{3+}$ complex, measured at pH 7.4 and room temperature, is further illustrated in FIG. 27. The curve depicts the best fit of a combination of MT theory and paramagnetic theory, presented in Equations 1 and 2, to the experimental data. This shows that substantial MT contrast may be obtained at concentrations similar to CA concentrations in clinical use. The results of FIG. 27 also illustrate that at a certain concentration of CA, the MT effect is independent of concentration. While not restricting the scope of the invention to a particular theory, it is believed that the magnitude of MT effect is strongly linked to the paramagnetic properties of the central metallic ions. That is, although the MT effect should be proportional to concentration at all concentrations, when the concentration gets too high, the spin lattice relaxation time of bulk water (T1sat) becomes too short and dominates the MT effect. For example, for the $Yb(9)^{3+}$ complex, at higher concentrations, paramagnetic relaxation effect due to $Yb^{3+}$ predominates at about 20 mM or higher. Under these conditions, there will be no further MT decrease because the saturated MT signal quickly recovers. As such, an optimal concentration is at about 20 mM of the $Yb(9)^{3+}$ complex. Of course, lower concentration of CA may be preferred for other reasons, such as minimizing the dose of CA necessary to administer to a subject. This experiment also suggests that conventional CAs, using metal ions such as $Gd^{3+}$ for example, will have an even greater effect on shortening T1sat, and therefore are unsuitable for producing MT-based contrast, even at very low concentrations.

Experiment 13

Experiment thirteen was conducted to examine the effect of pH on MT obtained using the lanthanide-macrocylic complexes of the present invention containing two exchangeable sites with different pH responses. Such complexes, for example $Eu(2)^-$ and $Yb(9)^{3+}$, may be used as pH-reporter-CAs in biological applications.

Figure 28:
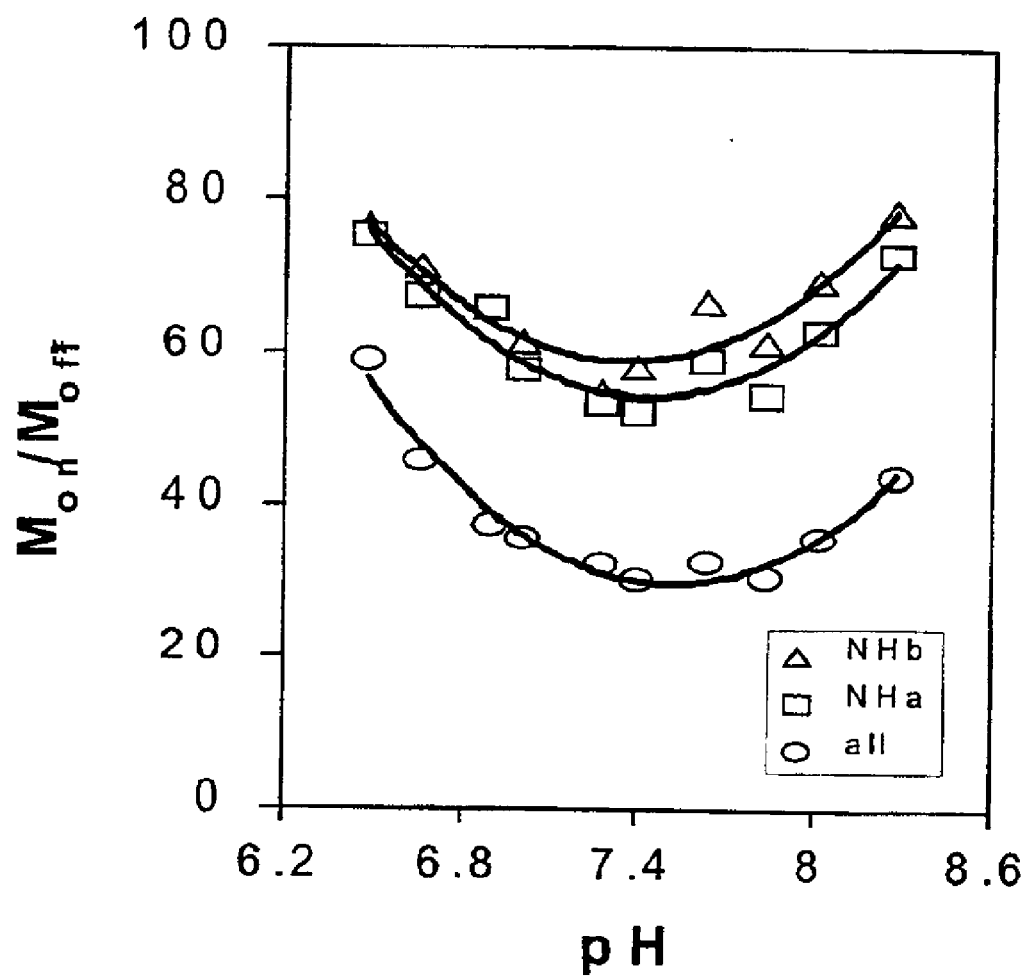
FIG. 28 illustrates an exemplary pH dependence of the MT effect obtained while applying a saturating radio frequency pulse at one or both of the resonance signal of the $H_a$ and $H_b$ associated with the amides in the pendent arms of the Yb(9)$^{3+}$ complex of the present invention.
Figure 29:
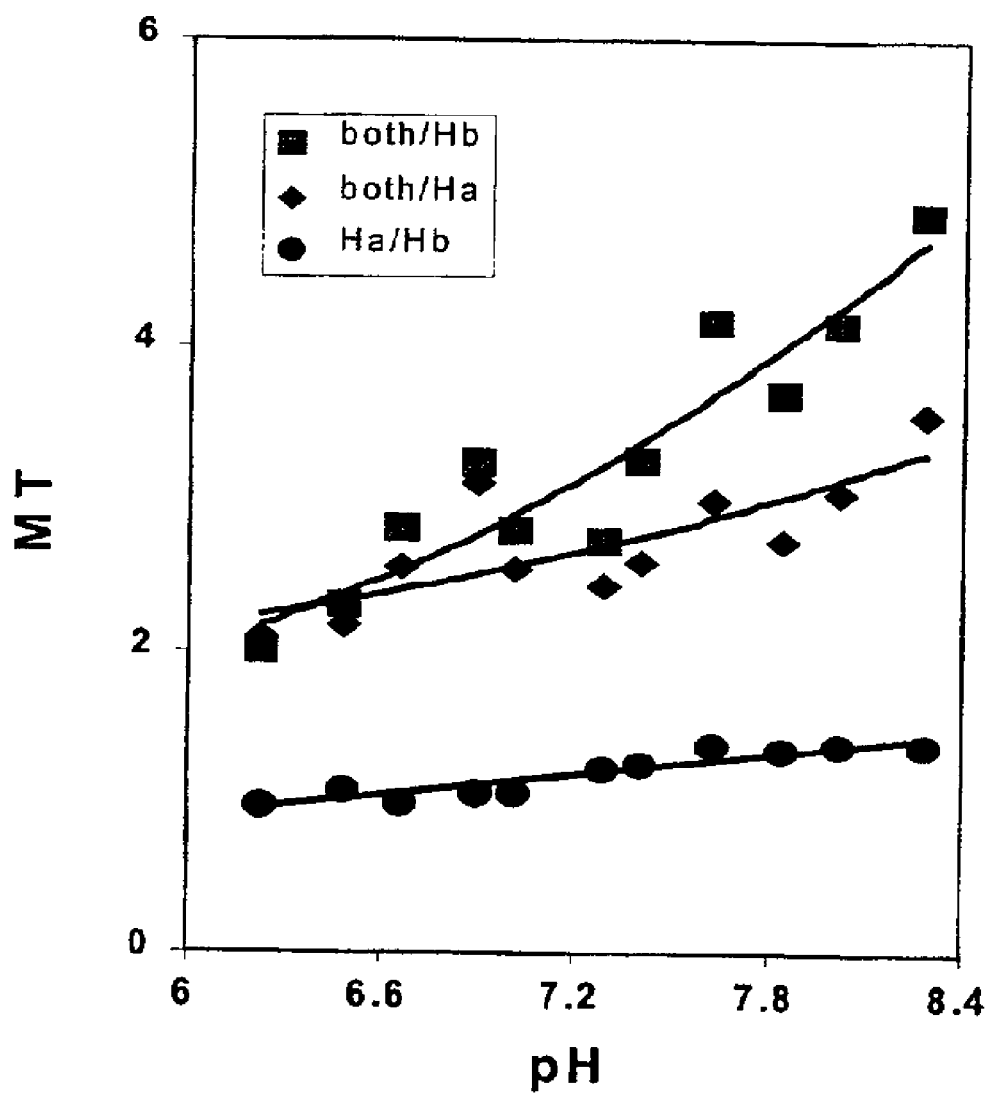
FIG. 29 illustrates an exemplary pH dependence of the MT ratios obtained while applying a saturating radio frequency pulse at one or both of the resonance signal of the $H_a$ and $H_b$ associated with the amides in the pendent arms of the Yb(9)$^{3+}$ complex of the present invention.

The pH dependence of MT obtained for an aqueous solution containing 30 mM $Yb(9)^{3+}$ at 25° C., is shown in FIG. 28. The saturating RF pulse was applied at the MR frequency of the amide protons ($M_{on}$), as described in Experiment 11, using either a bandwidth of 600 Hz when $H_a$ and $H_b$ were saturated individually (pwwet=7.5 ms and wetpwr=20 db), or a bandwidth of 1500 Hz when for saturating both amide protons simultaneously. Analogous data was collected with the same type of saturating pulse, but located on the opposite side and equal distance away from the bulk water MR signal ($M_{off}$) The symbols, Δ and o represent data points for saturating $H_a$, $H_b$ and both sites, respectively. Similar to that observed for $Eu(2)^-$, the relationship between pH and the extent of MT ($M_{on}/M_{off}$) is complex showing a minimum in MT at about pH 7.4. The same data, expressed as ratios of MT (MTR), are presented in FIG. 29. MTR is defined as $[1-M_{off}/M_{on}]_{site1}/[1-M_{off}/M_{on}]_{site2}$, where site 1 and site 2 refers to saturation applied to amide protons $H_a$ or $H_b$ or both sites, as indicated in the figure legend. To a first approximation MTR, is proportional to $[\tau_M]_{site2}/[\tau_M]_{site1}$. As illustrated in FIG. 29, MTR increases as a function of increasing pH.

Figure 30:
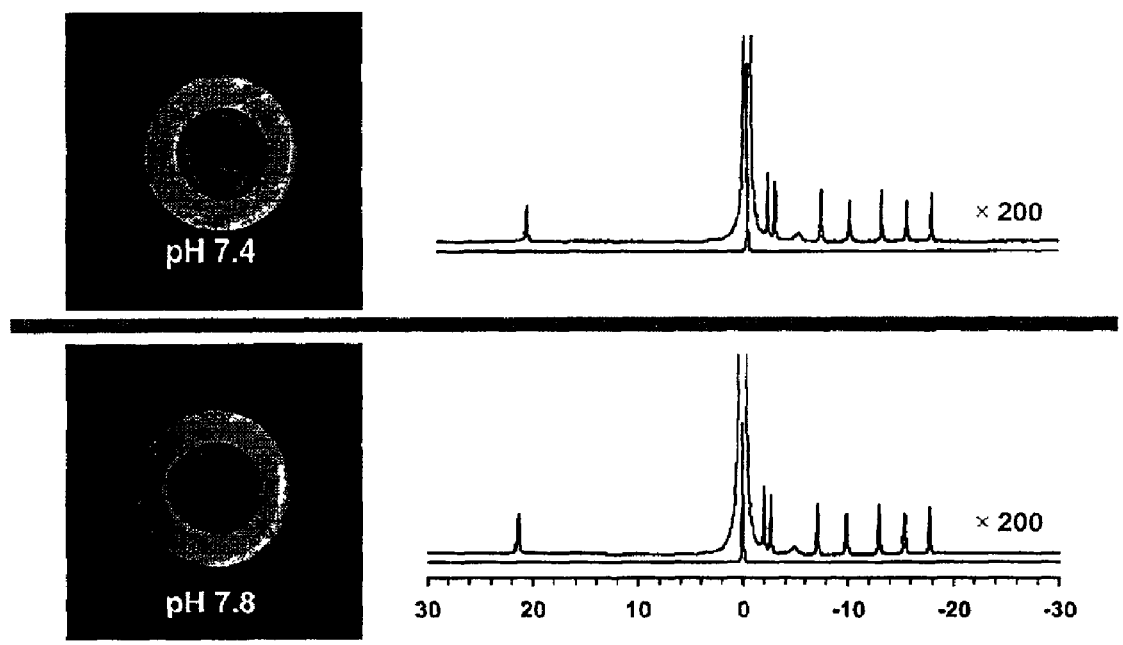
FIG. 30 illustrates exemplary $^1$H NMR spectra and MR images of a sample containing the Yb(9)$^{3+}$ complex (inner cylinder) produced according to the present invention in the presence of a saturating pulse at $\pm\Delta\omega$ for amides protons, $H_a$ and $H_b$, associated with the amides in the pendent arms of the complex at two different pHs.

FIG. 30 illustrates the effect of pH on MT images obtained while saturating the bound water of the $Eu(2)^-$ complex (62.5 mM) at 57 ppm, at pH 7.4 and pH 7.8, respectively. These data also illustrate that the NMR signal from the ligand, for example at about 21 ppm, are clearly visible and therefore may be used to determine the concentration of CA agent present in a sample. Because the lanthanide-macrocylic complexes of the present invention contain MR proton signals outside of the frequency range normally observed for biological molecules, it is possible to determine the concentration of such CAs in biological samples by measuring their $^1H$ NMR spectra. It follows therefore, that by measuring the CA's concentration, environmental parameters, such as pH, may be determined by analyzing MT image intensities and applying MT theory, as presented in equations 1 and 2, for example. In comparison, the $^1H$ NMR signals from conventional CA, containing $Gd^{3+}$ for example, are not visible and therefore can not be used as concentration markers.

Experiment 14

In Experiment 14 several other lanthanide-macrocylic complexes of the present invention were synthesized. For example, a lanthanide-macrocylic complex of the present invention was prepared having the general formula, $Ln(3)^{3+}$, where the four pendent arms R, R', R" and R"' are all phosphonate diethyl ester-acetamidoacetate (i.e., LnDOTA-4AmPE$^{3+}$), as depicted below:

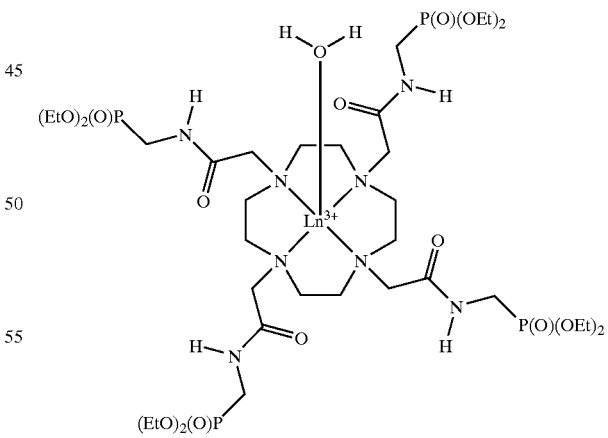

Another lanthanide-macrocylic complex of the present invention was prepared having the general formula, $Ln(4)^{5-}$, where the four pendent arms R, R', R" and R"' are all phosphonate-acetamidoacetate (i.e., LnDOTA-4AmP$^{5-}$), as depicted below:

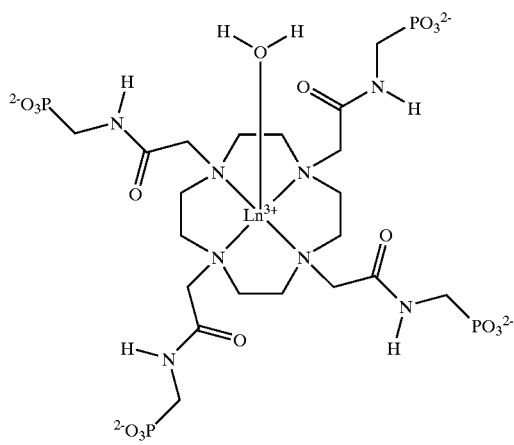

Yet another lanthanide-macrocylic complex of the present invention was prepared having the general formula, Ln(5)$^{3+}$, where the four pendent arms R, R', R" and R'" are all pyridine-acetamidoacetate (i.e., LnDOTA-4AmPy$^{3+}$), as depicted below:

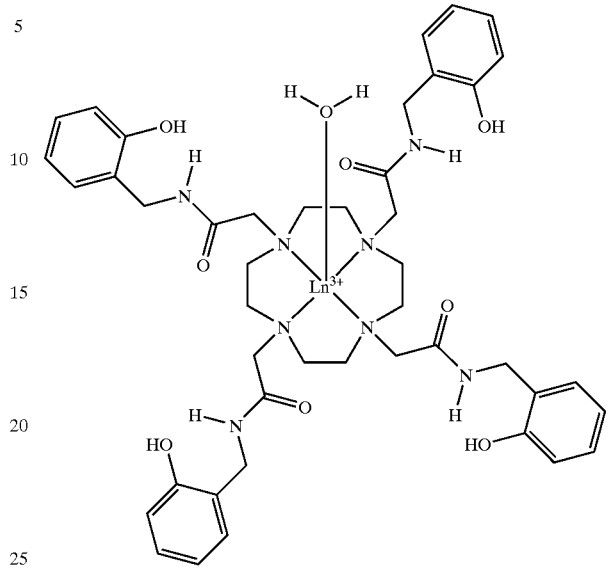

Another lanthanide-macrocylic complex of the present invention was prepared having the general formula, Ln(7)$^{3+}$, where the two pendent arms R' and R'" are phosphonate diethyl ester-acetamidoacetate and the other two pendent arms R and, R" are carboxyethyl-acetamidoacetate (i.e., LnDOTA-2AmCE-2AmPE$^{3+}$), as depicted below:

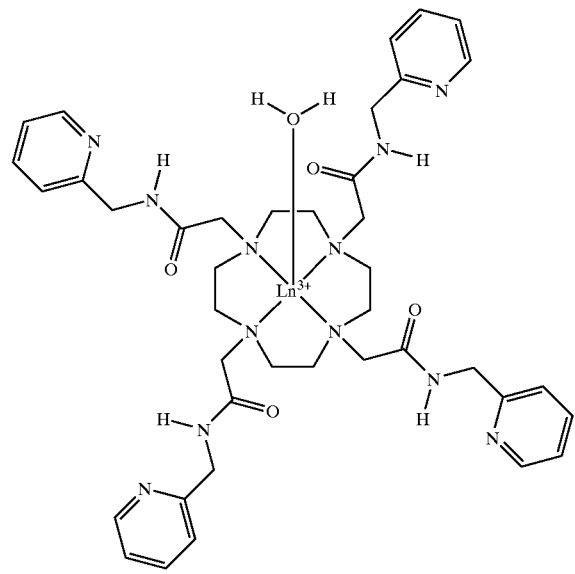

Still another lanthanide-macrocylic complex of the present invention was prepared having the general formula, Ln(6)$^{3+}$, where the four pendent arms R, R', R" and R'" are all phenol-acetamidoacetate (i.e., LnDOTA-4AmPhOH$^{3+}$), as depicted below:

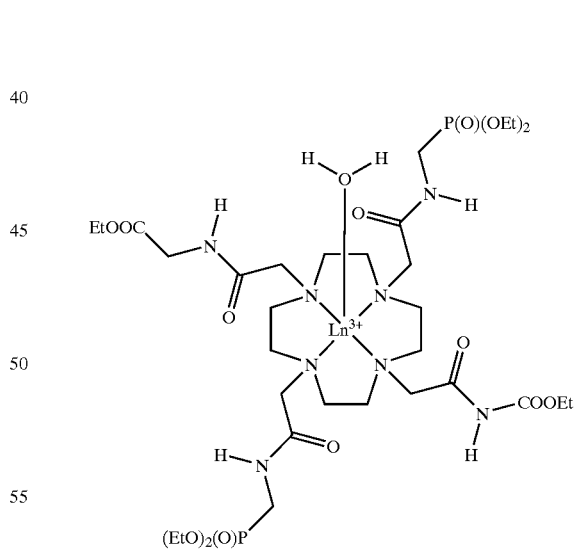

Another lanthanide-macrocylic complex of the present invention was prepared having the general formula, Ln(8)$^{3-}$, where the two pendent arms R' and R'" are phosphonate-acetamidoacetate and the other two pendent arms R and, R" are carboxyl-acetamidoacetate (i.e., LnDOTA-2AmC-2AmP$^{3-}$), as depicted below:

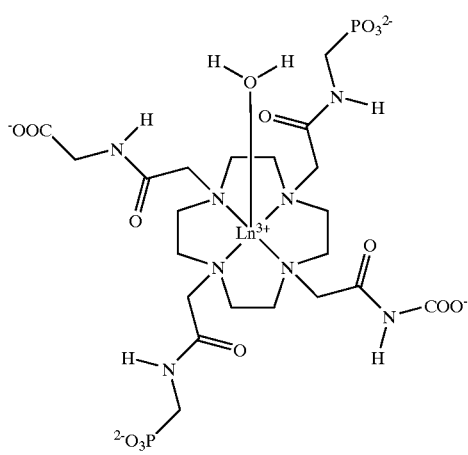

Although the present invention has been described in detail, those skilled in the art should understand that they can make various changes, substitutions and alterations herein without departing from the spirit and scope of the invention in its broadest form.

What is claimed is:

1. A chemical exchange saturation transfer contrast agent comprising:
a tetraazacyclododecane ligand having a general formula as follows:

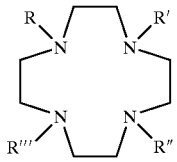

wherein pendent arms R, R', R" and R'" are amides having a general formula:
—$CR_1H$—CO—NH—$CH_2$—$R_2$, wherein $R_1$ is selected from the group consisting of:
H;
Alkyl groups having 20 carbon atoms or less;
Cycloalkyl groups having 20 carbon atoms or less;
Alkyloxy groups having 20 carbon atoms or less;
Alkyl ethers having 10 oxygen atoms or less and 20 carbon atoms or less; and
Polyols having 20 carbon atoms or less, and
$R_2$ is selected from the group consisting of:
—COOEt;
—COO⁻;
—POOEt;
—$PO_3^{-2}$;
pyridine; and
phenol;
a paramagnetic metal ion coordinated to said tetraazacyclododecane ligand wherein said paramagnetic metal is selected from the group consisting of:
$Eu^{3+}$;
$Tb^{3+}$;
$Dy^{3+}$;
$Ho^{3+}$;
$Pr^{3+}$;
$Nd^{3+}$;
$Sm^{3+}$;
$Er^{3+}$; and
$Tm^{3+}$; and a water molecule bound to said tetraazacyclododecane ligand and said paramagnetic metal ion wherein said water molecule has a $\Delta\omega \cdot \tau_M \geq 1$ and a $\Delta\omega \geq 6$ ppm.

2. The contrast agent as recited in claim 1 wherein said $\Delta\omega \geq 20$ ppm.

3. The contrast agent as recited in claim 1 wherein said $R_2$ does not have a proton exchangeable group.

4. A method of using a magnetic resonance (MR) chemical exchange saturation transfer contrast agent, comprising:
subjecting a contrast agent contained within a sample to a radio frequency pulse wherein said contrast agent is a tetraazacyclododecane ligand having a general formula of:

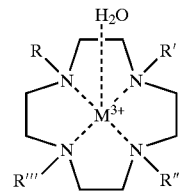

wherein pendent arms R, R', R" and R'" are amides having a general formula:
—$CR_1H$—CO—NH—$CH_2$—$R_2$, is selected from the group consisting of:
H;
Alkyl groups having 20 carbon atoms or less;
Cycloalkyl groups having 20 carbon atoms or less;
Alkyloxy groups having 20 carbon atoms or less;
Alkyl ethers having 10 oxygen atoms or less and 20 carbon atoms or less; and
Polyols having 20 carbon atoms or less, and
$R_2$ is selected from the group consisting of:
—COOEt:
—COO⁻;
—POOEt;
—$PO_3^{-2}$;
pyridine; and
phenol and said tetraazacyclododecane ligand further includes a paramagnetic metal ion ($M^{3+}$) coordinated to said tetraazacyclododecane ligand wherein said paramagnetic metal is selected from the group consisting of:
$Eu^{3+}$;
$Tb^{3+}$;
$Dy^{3+}$;
$Ho^{3+}$;
$Pr^{3+}$;
$Nd^{3+}$;
$Sm^{3+}$;
$Er^{3+}$; and
$Tm^{3+}$, and a water molecule ($H_2O$) bound to said tetraazacyclododecane ligand and said paramagnetic metal wherein said water molecule has a $\Delta\omega \cdot \tau_M \geq 1$ and a $\Delta\omega \geq 6$ ppm; and
obtaining a magnetization transfer signal by applying a radio frequency pulse at a resonance frequency of said water molecule.

5. The method as recited in claim 4 wherein said $\Delta\omega \geq 20$ ppm.

6. The method as recited in claim 4 further includes producing a magnetization transfer magnetic resonance image from said magnetization transfer signal.

7. The method as recited in claim 4 further includes applying said radio frequency pulse as a saturating pulse.

8. The method as recited in claim 4 wherein said pendent arms are identical.

9. The method as recited in claim 4 wherein said pendent arms R and R" are identical, said pendent arms R' and R'" are identical, and said pendent arms R' and R'" are not equal to said pendent arms R and R".

10. The method as recited in claim 4 further includes obtaining said magnetization transfer signal by applying a radio frequency pulse at a resonance frequency of said protons associated with said amide.

11. A magnetic resonance system, comprising:
a magnetic resonance (MR) chemical exchange saturation transfer contrast agent, wherein said MR agent tetraazacyclododecane ligand, having a general formula of:

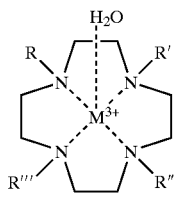

wherein pendent arms R, R', R" and R'" are amides having a general formula:
—$CR_1H$—CO—NH—$CH_2$—$R_2$, wherein $R_1$ is selected from the group consisting of;
H;
Alkyl groups having 20 carbon atoms or less;
Cycloalkyl groups having 20 carbon atoms or less;
Alkyloxy groups having 20 carbon atoms or less;
Alkyl ethers having 10 oxygen atoms or less and 20 carbon atoms or less; and
Polyols having 20 carbon atoms or less, and
$R_2$ is selected from the group consisting of:
—COOEt;
—COO$^-$;
—POOEt;
—$PO_3^{-2}$;
pyridine; and
phenol; phenol, and said tetraazacyclododecane ligand further includes a paramagnetic metal ion ($M^{3+}$) coordinated to said tetraazacyclododecane ligand wherein said paramagnetic metal is selected from the group consisting of:
$Eu^{3+}$;
$Tb^{3+}$;
$Dy^{3+}$;
$Ho^{3+}$;
$Pr^{3+}$;
$Nd^{3+}$;
$Sm^{3+}$;
$Er^{3+}$; and
$Tm^{3+}$, and a water molecule (H20) bound to said tetraazacyclododecane ligand and said paramagnetic metal wherein said water molecule has a $\Delta\omega \cdot \tau_M \geq 1$ and a $\Delta\omega \geq 6$ ppm, and wherein said MR contrast agent produces a magnetization transfer signal when subjected to a radio frequency pulse; and
a magnetic resonance apparatus configured to produce said frequency pulse.

12. The magnetic resonance system recited in claim 11, further comprising a sample containing said MR contrast agent.

13. The magnetic resonance system recited in claim 11, wherein said sample is a living subject.

14. The magnetic resonance system recited in claim 11, wherein said magnetic resonance apparatus produces a magnetization transfer image of said sample from said magnetization transfer signal.

15. The magnetic resonance system recited in claim 14, wherein said magnetic resonance apparatus produces said magnetization transfer image by applying said radio frequency pulse at a resonance frequency of said water molecule.

16. The magnetic resonance system recited in claim 15, wherein said magnetic resonance apparatus produces a magnetization transfer difference image by applying said radio frequency pulse at a $\Delta\omega$ of said water molecule, acquiring said magnetization transfer signal and subtracting said signal from a MR signal obtained by applying a radio frequency pulse at $-\Delta\omega$.

17. The magnetic resonance system recited in claim 14, wherein said magnetic resonance apparatus produces said magnetization transfer image by applying said radio frequency pulse at a resonance frequency of protons associated with an amide included in one or more of said pendent arms.

18. The magnetic resonance system recited in claim 11, wherein said radio frequency pulse is produced by said magnetic resonance apparatus and is a saturating pulse.

19. The magnetic resonance system recited in claim 11, wherein said saturating pulse is applied at a resonance frequency of said water molecule.

20. The magnetic resonance system recited in claim 11, wherein said saturating pulse ranges from about 1 to about 3 seconds.

21. The magnetic resonance system recited in claim 11 wherein said water molecule has a $\Delta\omega \cdot \tau_M \geq 4$.

22. The magnetic resonance system recited in claim 11 wherein said $\Delta\omega \geq 20$ ppm.

23. The magnetic resonance system recited in claim 11 wherein said $\Delta\omega \cdot \tau_M \geq 1$ occurs at a temperature of at least about 22° C.

* * * * *